US010263190B2

United States Patent
Yan et al.

(10) Patent No.: US 10,263,190 B2
(45) Date of Patent: Apr. 16, 2019

(54) DIFLUOROBITHIOPHENE-BASED DONOR-ACCEPTOR POLYMERS FOR ELECTRONIC AND PHOTONIC APPLICATIONS

(71) Applicant: THE HONG KONG UNIVERSITY OF SCIENCE AND TECHNOLOGY, Hong Kong (CN)

(72) Inventors: He Yan, Hong Kong (CN); Zhengke Li, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 30 days.

(21) Appl. No.: 15/516,792

(22) PCT Filed: Oct. 22, 2015

(86) PCT No.: PCT/CN2015/092530
§ 371 (c)(1),
(2) Date: Apr. 4, 2017

(87) PCT Pub. No.: WO2016/062258
PCT Pub. Date: Apr. 28, 2016

(65) Prior Publication Data
US 2017/0301862 A1   Oct. 19, 2017

Related U.S. Application Data

(60) Provisional application No. 62/122,479, filed on Oct. 22, 2014.

(51) Int. Cl.
*H01B 1/12* (2006.01)
*H01L 51/00* (2006.01)
(Continued)

(52) U.S. Cl.
CPC ........ *H01L 51/0036* (2013.01); *C07D 333/28* (2013.01); *C07D 417/14* (2013.01);
(Continued)

(58) Field of Classification Search
CPC ............. H01L 51/0036; H01L 51/0043; H01L 51/0046; H01L 51/0047; H01L 51/0566; H01L 51/4253; C07D 417/14; C07D 333/28; C07F 7/2212; C07F 7/2208; C08K 3/045; C08G 61/122; C08G 61/123; C08G 61/124; C08G 61/126; C08G 2261/3246; C08G 2261/41; C08G 2261/92;
(Continued)

(56) References Cited

PUBLICATIONS

Chemical Abstracts Registry No. 1385674-50-9 (2012) (Year: 2012).*
(Continued)

*Primary Examiner* — Mark Kopec
*Assistant Examiner* — Jaison P Thomas
(74) *Attorney, Agent, or Firm* — Nath, Goldbgerg & Meyer; Joshua B. Goldberg; Scott H. Blackman

(57) ABSTRACT

An organic compound, a donor-acceptor conjugated polymer, a formulation and a thin film, wherein a solution of the donor-acceptor conjugated polymer exhibits a peak optical absorption spectrum red shift of at least 100 nm when the donor-acceptor conjugated polymer solution is cooled from 140° C. to room temperature.

16 Claims, 2 Drawing Sheets

(51) Int. Cl.
*C07F 7/22* (2006.01)
*C08G 61/12* (2006.01)
*C08K 3/04* (2006.01)
*C07D 333/28* (2006.01)
*C07D 417/14* (2006.01)
*H01L 51/42* (2006.01)

(52) U.S. Cl.
CPC .......... *C07F 7/2208* (2013.01); *C08G 61/122* (2013.01); *C08G 61/123* (2013.01); *C08G 61/124* (2013.01); *C08G 61/126* (2013.01); *C08K 3/045* (2017.05); *H01B 1/127* (2013.01); *C08G 2261/124* (2013.01); *C08G 2261/146* (2013.01); *C08G 2261/1412* (2013.01); *C08G 2261/18* (2013.01); *C08G 2261/3223* (2013.01); *C08G 2261/3241* (2013.01); *C08G 2261/3246* (2013.01); *C08G 2261/334* (2013.01); *C08G 2261/344* (2013.01); *C08G 2261/364* (2013.01); *C08G 2261/41* (2013.01); *C08G 2261/414* (2013.01); *C08G 2261/91* (2013.01); *C08G 2261/92* (2013.01); *H01L 51/0047* (2013.01); *H01L 51/4253* (2013.01); *Y02E 10/549* (2013.01)

(58) Field of Classification Search
CPC .......... C08G 2261/334; C08G 2261/18; C08G 2261/146; C08G 2261/1412; C08G 2261/124; C08G 2261/3223; C08G 2261/364; C08G 2261/414; C08G 2261/91; C08G 2261/3241; C08G 2261/344; Y02E 10/549; H01B 1/127
See application file for complete search history.

(56) References Cited

PUBLICATIONS

Jo et al. "Comparison of Two D-A Type Polymers with Each Being Fluorinated on D and A Unit for High Performance Solar Cells" Adv. Funct. Mater. 25, 120-125 (2015) (Year: 2015).*
Liu et al., "Aggregation and morphology control enables multiple cases of high-efficiency polymer solar cells," Nat. Commun. 5:5293 doi: 10.1038/ncomms6293 (2014) (Year: 2014).*
Li et al., "Dramatic performance enhancement for large bandgap thick-film polymer solar cells introduced by a difluorinated donor unit," Nano Energy, 15, 607-615 (2015) (Year: 2015).*
Jung, et al., "Fluoro-Substituted n-Type Conjugated Polymers for Additive-Free All-Polymer Bulk Heterojunction Solar Cells with High Power Conversion Efficiency of 6.71%," Adv. Mater. 27, pp. 3310-3317 (2015) (Year: 2015).*
Kok-Haw Ong, et al. "Design and synthesis of benzothiadiazole-oligothiophene polymers for organic solar cell applications", Polymer Chemistry, vol. 4, No. 6, Dec. 18, 2012, p. 1863.
Jea Woong Jo, et al. "Fluorination of Polythiophene Derivatives for High Performance Organic Photovoltaics", Chemistry of Materials, vol. 26, No. 14, Jul. 7, 2014, pp. 4214-4220.
Jordi Casanovas, et al. "Properties of Poly(3-halidethiophene)s" Physical Chemistry Chmical Physics., vol. 14, No. 28. Jun. 14, 2012, p. 10050.
Extended European Search Report dated Jun. 4, 2018 in corresponding European Patent Application No. 15853053.5.

* cited by examiner

DIFLUOROBITHIOPHENE-BASED DONOR-ACCEPTOR POLYMERS FOR ELECTRONIC AND PHOTONIC APPLICATIONS

This is a National Phase Application filed under 35 U.S.C. 371 as a national stage of PCT/CN2015/092530, filed Oct. 22, 2015, an application claiming the benefit of provisional U.S. Patent Application No. 62/122,479 filed Oct. 22, 2014, which was filed by the inventor hereof, the content of each of which is hereby incorporated by reference in its entirety.

RELATED APPLICATIONS

The present patent application claims priority to provisional U.S. Patent Application No. 62/122,479 filed Oct. 22, 2014, which was filed by the inventor hereof and is incorporated by reference herein in its entirety.

TECHNICAL FIELD

The present subject matter relates to novel organic compounds, donor-acceptor conjugated polymers, methods for their preparation and intermediates used therein, the use of formulations containing such polymers as semiconductors in organic electronic (OE) devices, especially in organic photo voltaic (OPV) and organic field-effect transistor (OFET) devices, and to OE and OPV devices made from these formulations.

BACKGROUND

In recent years there has been growing interest in the use of organic semiconductors, including conjugated polymers, for various electronic applications.

One particular area of importance is the field of organic photo voltaics (OPV). Organic semiconductors (OSCs) have found use in OPV as they allow devices to be manufactured by solution-processing techniques such as spin casting and printing. Solution processing can be carried out cheaper and on a larger scale compared to the evaporative techniques used to make inorganic thin film devices. State-of-the-art OPV cells consist of a blend film of a conjugated polymer and a fullerene derivative. Recent improvements in the efficiencies of single-junction OPVs, Yu et al., *Nat. Photonics* 2014, 8, 716. (efficiency ~8-9%), have largely been due to the development of low-band-gap polymers, which are defined as polymers with an absorption onset of at least 750 nm or more and with a band-gap of 1.65 eV or less. (For example, a low-performance OPV polymer, P3HT, (bandgap ~1.9 eV) is not considered the state-of-the-art polymers for OPVs.)

The polymers commonly used in PSCs consist of an electron donating (donor or D) and an electron accepting (acceptor or A) comonomer units. It is convenient to use such a D-A alternating copolymer strategy to obtain polymers with low optical bandgaps as the HOMO level of the polymer is mostly located on the donor unit and the LUMO level mostly on the acceptor unit. The commonly accepted model developed by Brabec, etc. indicates that elaborately designed HOMO and LUMO energy level is a basic requirement for high-performance polymer solar cell because open-circuit voltage ($V_{oc}$) of polymer solar cells is determined by the difference between the HOMO level of the polymer and the LUMO level of the fullerene derivative. LUMO energy level is relatively more important because LUMO offset between polymer and fullerene should be small enough to minimize $V_{oc}$ loss. By modifying the acceptor unit with electron-donating or withdrawing groups, the LUMO level of the D-A polymer can be effectively tuned, while the same can be done to tune the HOMO level by modifying the donor unit.

In the area of conjugated polymers for PSCs, fluorination method has been used to modify conjugated polymers to tune the HOMO and LUMO levels. There are several reports on fluorinating the acceptor unit of the D-A conjugated polymers, which turns out to be an effective method to adjust the energy levels of conjugated polymers accompanied by other positive effects including enhanced polymer stacking ability and crystallinity. For example, You et al., *J. Am. Chem. Soc.* 2013, 135, 1806, reported that difluorination of benzothiadizole unit lead to lower HOMO level and thus enhanced $V_{oc}$ of the solar cell as well as increased polymer stacking in the solid state. In contrast, there were few successful attempts in fluorinating the donor part of D-A conjugated polymers, which has yielded improved performance for the PSC devices. It was believed in one case that a perfluorinated polymer backbone (with fluorine on both the donor and accept units) lead to poor PSC performance attribute to too strong self-organization property and fluorophobicity effect of the polymer.

SUMMARY

The present subject matter provides an organic compound of the following formula:

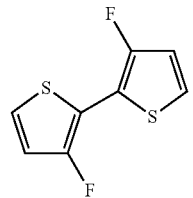 [SMILES: Fc1ccsc1-c1sccc1F]

The present subject further relates to a donor-acceptor conjugated polymer comprising one or more repeating units of the following formula:

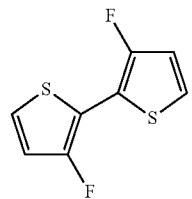

The present subject matter further provides a donor-acceptor conjugated polymer comprising at least one or more repeating units having a formula of:

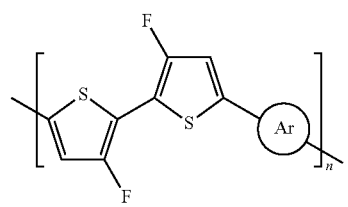

wherein Ar is an aromatic group independently selected from the group consisting of the following units:

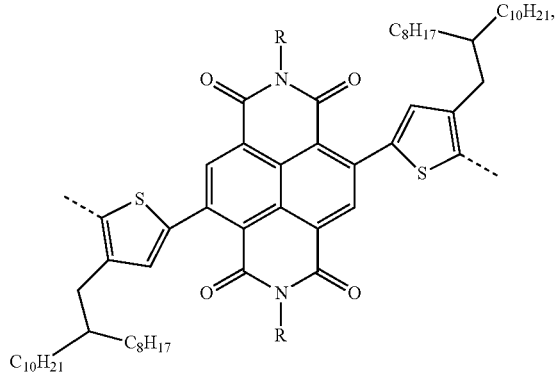

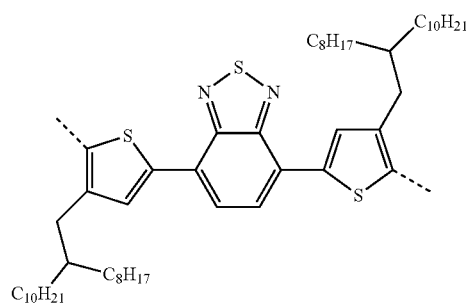

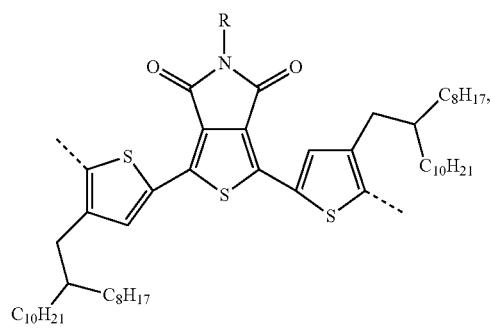

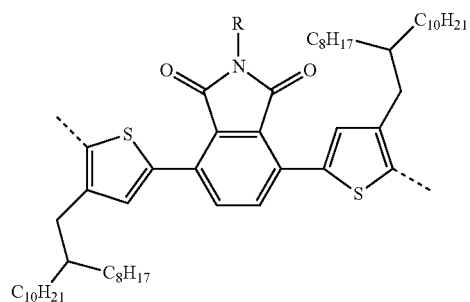

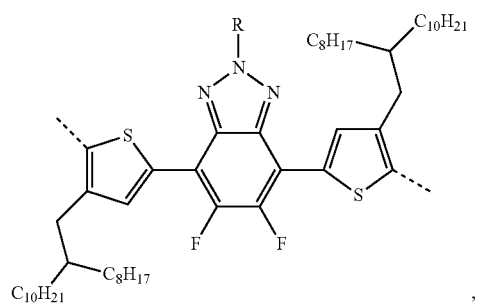

, and

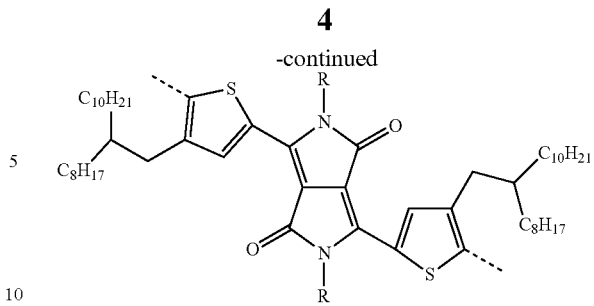

each R is independently selected from the group consisting of straight-chain, branched, and cyclic alkyl with 2-40 C atoms, wherein one or more non-adjacent C atoms are optionally replaced by —O—, —S—, —C(O)—, —C(O—)—O—, —O—C(O)—, —O—C(O)—O—, —CR$^0$=CR$^{00}$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein R$^0$ and R$^{00}$ are independently a straight-chain, branched, or cyclic alkyl group. In some embodiments, the Ar group contains two or aromatic rings.

The present subject matter further relates to a donor-acceptor conjugated polymer having an average molecular weight from 20,000 to 40,000 gram/mole.

The donor-acceptor conjugated polymer of the present subject matter shows a dramatic red shift (>100 nm) in the peak of its optical absorption spectrum when the polymer solution is cooled from high temperatures (e.g., 140° C.) to room temperature, which surprisingly is related to the excellent polymer/fullerene morphology formed by the donor-acceptor conjugated polymer.

The present subject matter further relates to the use of a formulation comprising an organic solvent, a fullerene and a donor-acceptor conjugated polymer as described above and below.

The present subject matter further relates to the use of a formulation as described above and below as a coating or printing ink, especially for the preparation of OE devices and rigid or flexible organic photo voltaic (OPV) cells and devices.

The present subject matter further relates to an OE device prepared from a formulation as described above and below. The OE devices contemplated in this regard include, without limitation, organic field effect transistors (OFET), integrated circuits (IC), thin film transistors (TFT), Radio Frequency Identification (RFID) tags, organic light emitting diodes (OLED), organic light emitting transistors (OLET), electro luminescent displays, organic photo voltaic (OPV) cells, organic solar cells (O-SC), flexible OPVs and O—SCs, organic laser diodes (O-laser), organic integrated circuits (O-IC), lighting devices, sensor devices, electro dematerials, photo conductors, photo detectors, electro photo graphic recording devices, capacitors, charge injection layers, Schottky diodes, planarising layers, antistatic films, conducting substrates, conducting patterns, photo conductors, electro photographic devices, organic memory devices, biosensors and biochips.

The present subject matter further provides a thin film comprising a donor-acceptor conjugated polymer and a fullerene as above and below described.

Donor-acceptor conjugated polymers with such structures were found to show good processability and high solubility in organic solvents, and are thus especially suitable for large scale production using solution processing methods. At the same time, they show a low bandgap, high charge carrier mobility, high external quantum efficiency in BHJ solar cells, good morphology when combined with over a dozen fullerenes, and are promising materials for organic electronic OE devices, especially for OPV devices with high power conversion efficiency.

The compounds, formulations, methods and devices of the present subject matter provide surprising improvements in the efficiency of the OE devices and the production thereof. Unexpectedly, the performance, the lifetime and the efficiency of the OE devices can be improved, if these devices are achieved by using a formulation of the present subject matter. Furthermore, the formulation of the present subject matter provides good film-forming properties. Especially, the homogeneity and the quality of the films can be improved. In addition thereto, the present subject matter enables better solution printing of OE devices, especially OPV devices.

BRIEF DESCRIPTION OF THE DRAWINGS

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

DETAILED DESCRIPTION

Definitions

Figure 1:
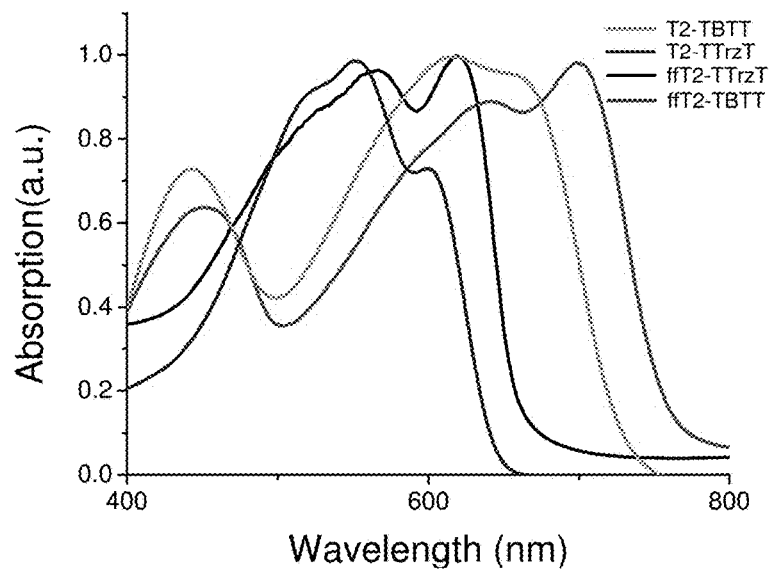
FIG. 1 shows the UV-V is spectra of a polymer in thin film according to one embodiment of the present subject matter.
Figure 2:
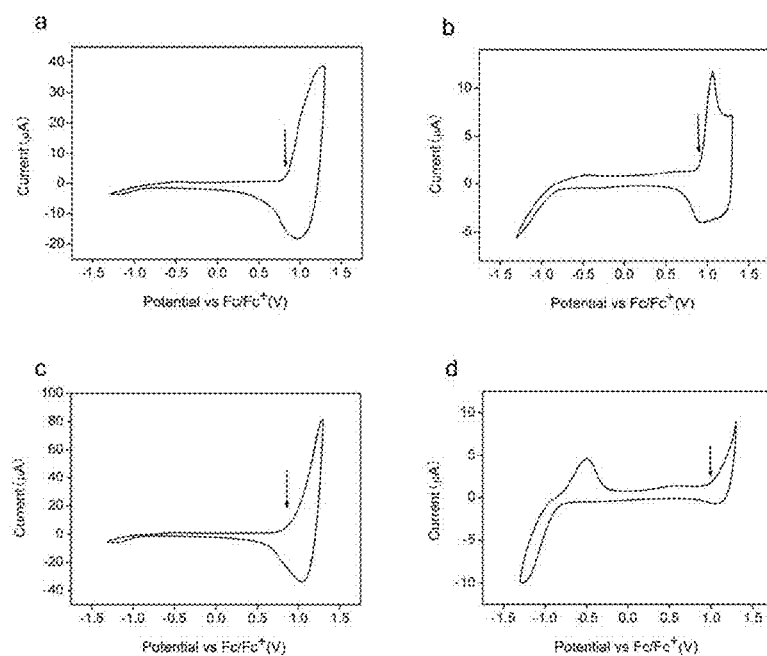
FIG. 2a-d shows the cyclic voltammetry plot of a polymer in 0.1 M (n-Bu)4N+PF6-acetonitrile solution according to the present teaching measurement.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "p-type semiconductor material" or a "donor" material refers to a semiconductor material, for example, an organic semiconductor material, having holes as the majority current or charge carriers. In some embodiments, when a p-type semiconductor material is deposited on a substrate, it can provide a hole mobility in excess of about $10^{-5}$ cm/Vs. In the case of field-effect devices, a p-type semiconductor also can exhibit a current on/off ratio of greater than about 10.

As used herein, an "n-type semiconductor material" or an "acceptor" material refers to a semiconductor material, for example, an organic semiconductor material, having electrons as the majority current or charge carriers. In some embodiments, when an n-type semiconductor material is deposited on a substrate, it can provide an electron mobility in excess of about $10^{-5}$ cm/Vs. In the case of field-effect devices, an n-type semiconductor also can exhibit a current on/off ratio of greater than about 10.

As used herein, "mobility" refers to a measure of the velocity with which charge carriers, for example, holes (or units of positive charge) in the case of a p-type semiconductor material and electrons (or units of negative charge) in the case of an n-type semiconductor material, move through the material under the influence of an electric field. This parameter, which depends on the device architecture, can be measured using a field-effect device or space-charge limited current measurements.

As used herein, a compound can be considered "ambient stable" or "stable at ambient conditions" when a transistor incorporating the compound as its semi conducting material exhibits a carrier mobility that is maintained at about its initial measurement when the compound is exposed to ambient conditions, for example, air, ambient temperature, and humidity, over a period of time. For example, a compound can be described as ambient stable if a transistor incorporating the compound shows a carrier mobility that does not vary more than 20% or more than 10% from its initial value after exposure to ambient conditions, including, air, humidity and temperature, over a 3 day, 5 day, or 10 day period.

As used herein, fill factor (FF) is the ratio (given as a percentage) of the actual maximum obtainable power, (Pm or Vmp*Jmp), to the theoretical (not actually obtainable) power, (Jsc*Voc). Accordingly, FF can be determined using the equation:

$$FF=(Vmp*Jmp)/(Jsc*Voc)$$

where Jmp and Vmp represent the current density and voltage at the maximum power point (Pm), respectively, this point being obtained by varying the resistance in the circuit until J*Vis at its greatest value; and Jsc and Voc represent the short circuit current and the open circuit voltage, respectively. Fill factor is a key parameter in evaluating the performance of solar cells. Commercial solar cells typically have a fill factor of about 0.60% or greater.

As used herein, the open-circuit voltage (Voc) is the difference in the electrical potentials between the a node and the cathode of a device when there is no external load connected.

As used herein, the power conversion efficiency (PCE) of a solar cell is the percentage of power converted from absorbed light to electrical energy. The PCE of a solar cell can be calculated by dividing the maximum power point (Pm) by the input light irradiance (E, in W/m2) under standard test conditions (STC) and the surface area of the solar cell (Ac in m2). STC typically refers to a temperature of 25° C. and an irradiance of 1000 W/m2 with an air mass 1.5 (AM 1.5) spectrum.

As used herein, a component (such as a thin film layer) can be considered "photo active" if it contains one or more compounds that can absorb photons to produce excitons for the generation of a photo current.

As used herein, "solution-processable" refers to compounds (e.g., polymers), materials, or compositions that can be used in various solution-phase processes including spin-coating, printing (e.g., inkjet printing, gravure printing, offset printing and the like), spray coating, electro spray coating, drop casting, dip coating, blade coating, and the like.

As used herein, a "semicrystalline polymer" refers to a polymer that has an inherent tendency to crystallize at least partially either when cooled from a melted state or deposited from solution, when subjected to kinetically favorable conditions such as slow cooling, or low solvent evaporation rate and so forth. The crystallization or lack thereof can be readily identified by using several analytical methods, for example, differential scanning calorimetry (DSC) and/or X-ray diffraction (XRD).

As used herein, "annealing" refers to a post-deposition heat treatment to the semicrystalline polymer film in ambient or under reduced/increased pressure for a time duration of more than 100 seconds, and "annealing temperature" refers to the maximum temperature that the polymer film is exposed to for at least 60 seconds during this process of annealing. Without wishing to be bound by any particular theory, it is believed that annealing can result in an increase of crystallinity in the polymer film, where possible, thereby increasing field effect mobility. The increase in crystallinity can be monitored by several methods, for example, by comparing the differential scanning calorimetry (DSC) or X-ray diffraction (XRD) measurements of the as-deposited and the annealed films.

As used herein, a "polymeric compound" (or "polymer") refers to a molecule including a plurality of one or more repeating units connected by covalent chemical bonds. A polymeric compound can be represented by General Formula I:

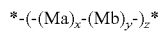   General Formula I wherein each Ma and Mb is a repeating unit or monomer. The polymeric compound can have only one type of repeating unit as well as two or more types of different repeating units. When a polymeric compound has only one type of repeating unit, it can be referred to as a homopolymer. When a polymeric compound has two or more types of different repeating units, the term "copolymer" or "copolymeric compound" can be used instead. For example, a copolymeric compound can include repeating units where Ma and Mb represent two different repeating units. Unless specified otherwise, the assembly of the repeating units in the copolymer can be head-to-tail, head-to-head, or tail-to-tail in addition, unless specified otherwise, the copolymer can be a random copolymer, an alternating copolymer, or a block copolymer. For example, General Formula I can be used to represent a copolymer of Ma and Mb having x mole fraction of Ma and y mole fraction of Mb in the copolymer, where the manner in which comonomers Ma and Mb is repeated can be alternating, random, regiorandom, regioregular, or in blocks, with up to z comonomers present. In addition to its composition, a polymeric compound can be further characterized by its degree of polymerization (n) and molar mass (e.g., number average molecular weight (M) and/or weight average molecular weight (Mw) depending on the measuring technique(s)).

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group." Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicycliccycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C6F5), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (0), nitrogen (N), sulfur (S), silicon (Si), and selenium (Se) or a polycyclic ring system where at least one of the rings present in the ring system is aromatic and contains at least one ring heteroatom. Polycyclicheteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine Noxidethiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), SiH2, SiH (alkyl), Si (alkyl)2, SiH (arylalkyl), Si (arylalkyl)2, or Si (alkyl) (arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

In the present subject matter, one or more of the above aims can be achieved by providing an organic compound of the following formula:

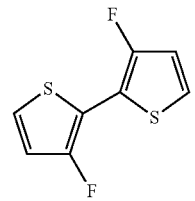 [SMILES: Fc1ccsc1-c1sccc1F]

In another exemplary embodiment, the present subject further relates to a donor-acceptor conjugated polymer comprising one or more repeating units of the following formula:

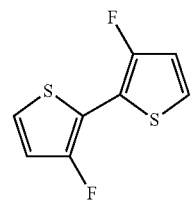

In yet another example embodiment, the present subject further relates to a donor-acceptor conjugated polymer having at least one or more repeating units containing the following building block:

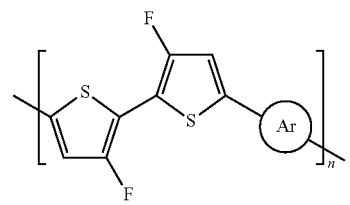

wherein Ar is as defined herein.

Figure 3:
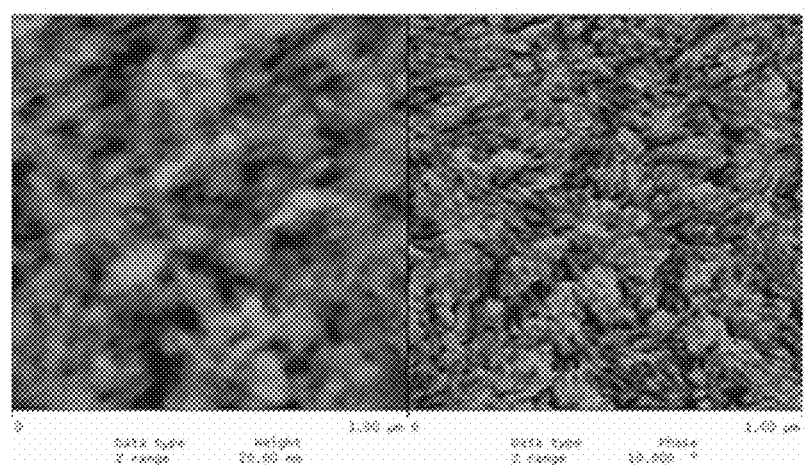
FIG. 3 displays the AFM surface topography and phase images of blend films containing different fullerenes and a polymer of the present teaching.

It was surprisingly found polymers containing such building blocks exhibit a dramatic red shift (>100 nm) in the peak of their optical absorption spectrum when a polymer solution containing the same is cooled from high temperatures (e.g., 140° C.) to room temperature. Surprisingly and beneficially, polymers exhibiting such absorption properties tend to form optimal polymer/fullerene morphology with many different fullerenes, as evidenced by the AFM images of many different polymer/fullerene films (FIG. 3). As a result of the excellent polymer/fullerene morphology based on such polymers, high-efficiency (9%) OPV devices were achieved using many fullerenes other than $PC_{71}BM$.

Polymer solutions are typically prepared in solvents such as dichlorobenzene at a concentration of 0.1 mg/mL. Upon heating to 140° C., a polymer of the present teaching shows UV-Vis absorption peak at 550 nm. Cooling of the polymer solution to room temperature led to a dramatic shift of the peak absorption to about 740 nm.

In one embodiment in this regard, the donor-acceptor conjugated polymer can comprise one or more repeating units of the following formula:

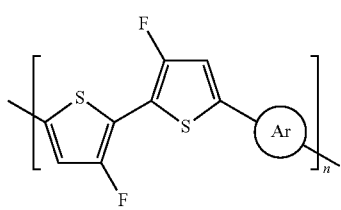

wherein Ar is an aromatic group independently selected from the group consisting of:

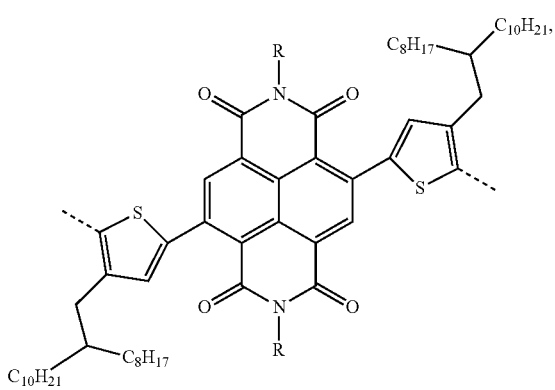

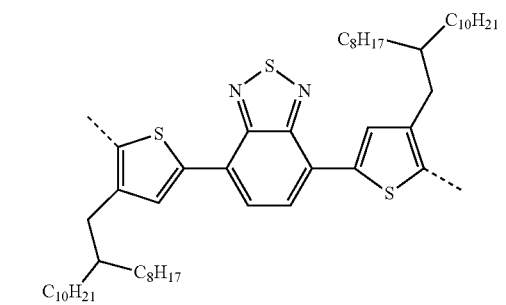

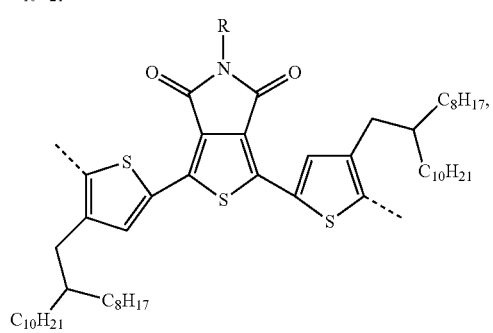

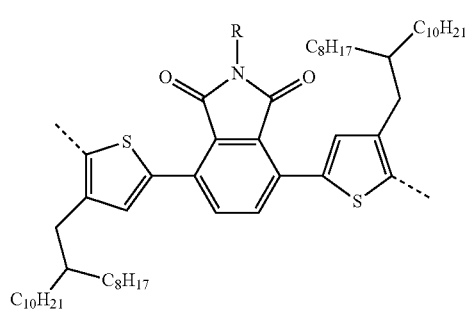

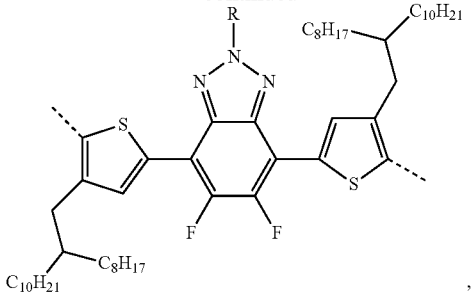

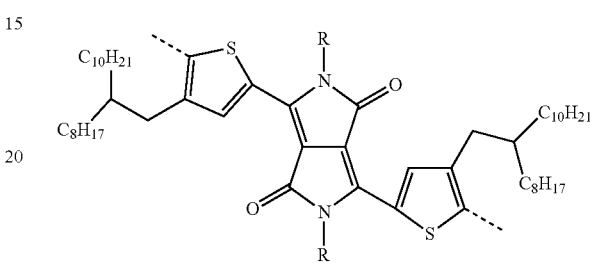
, and wherein each R is independently selected from the group consisting of straight-chain, branched, and cyclic alkyl with 2-40 C atoms, wherein one or more non-adjacent C atoms are optionally replaced by —O—, —S—, —C(O)—, —C(O)—O—, —O—C(O)—, —O—C(O)—O—, —CR$^o$=CR$^{oo}$—, —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein R$^o$ and R$^{oo}$ are independently a straight-chain, branched, or cyclic alkyl group. In a preferred embodiment, the Ar group contains two or more aromatic rings.

In another embodiment, the average molecular weight of the donor-acceptor conjugated polymer is in a range from 20,000 to 40,000 gram/mole.

In yet another embodiment, a solution of the donor-acceptor conjugated polymer exhibits a peak optical absorption spectrum red shift of at least 100 nm when the conjugated polymer solution is cooled from 140° C. to room temperature.

In another exemplary embodiment, a solution of the donor-acceptor conjugated polymer exhibits a peak optical absorption spectrum red shift at about 740 nm when the conjugated polymer solution is cooled from 140° C. to room temperature.

In another exemplary embodiment, the donor-acceptor conjugated polymer is further characterized in that it has an optical bandgap of 1.65 eV or lower.

In some embodiments, the formulation is further characterized in that the donor-acceptor conjugated polymer comprises one or more repeating units selected from the group consisting of:

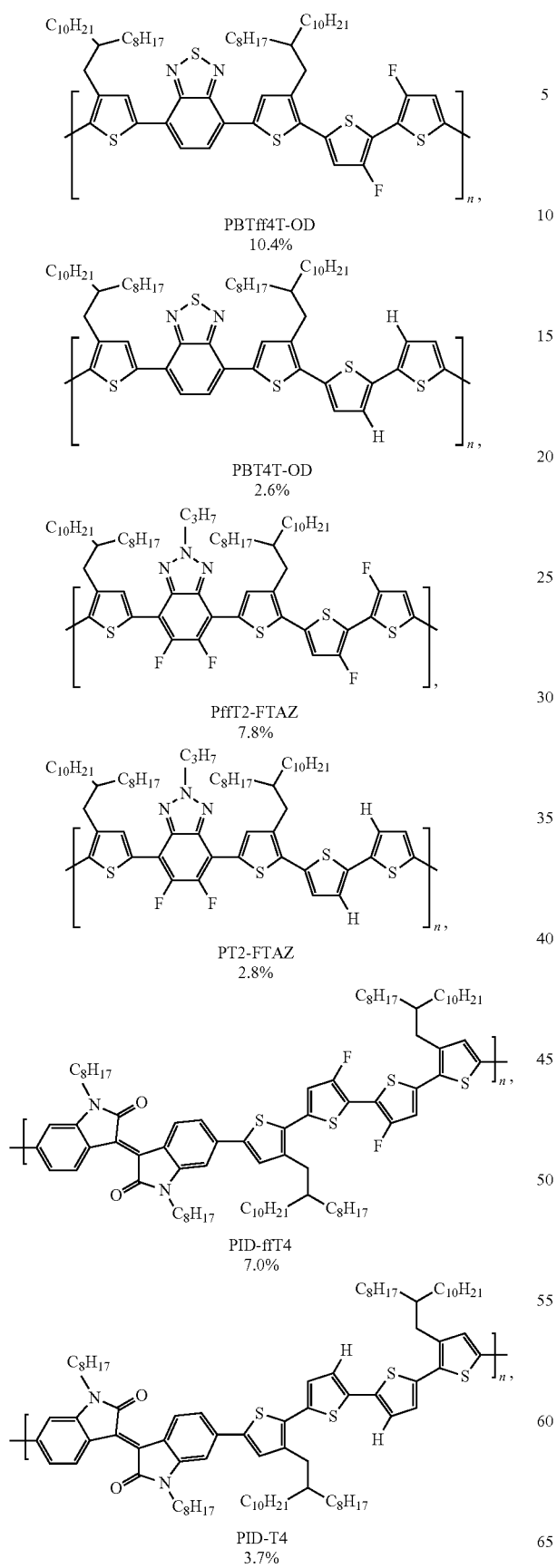
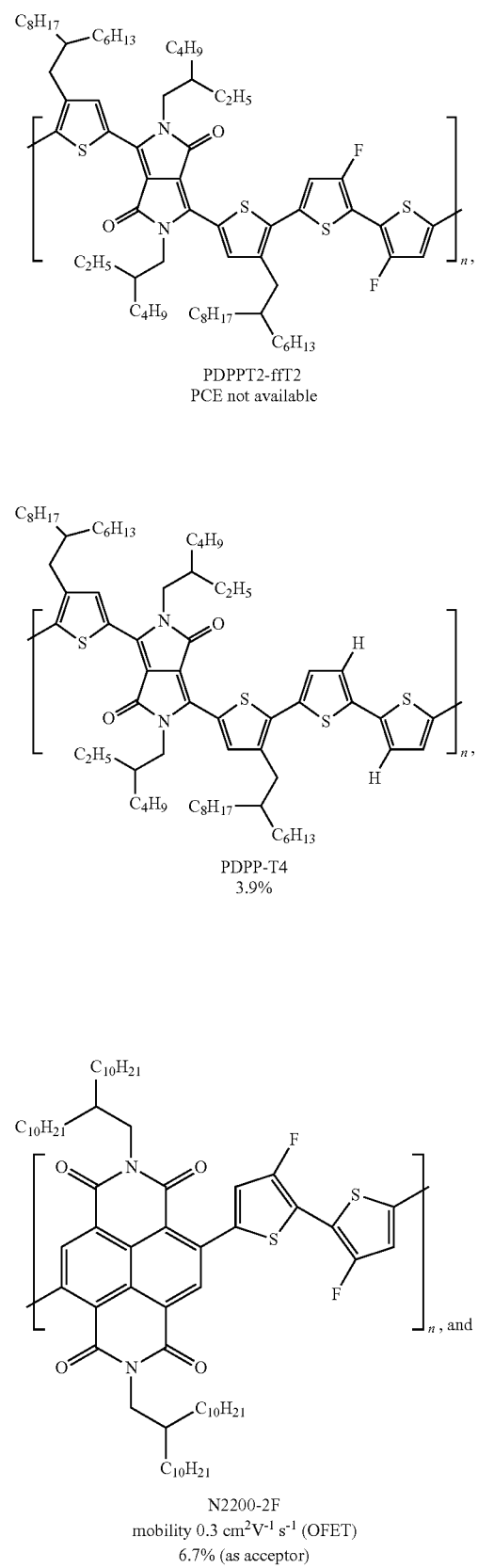

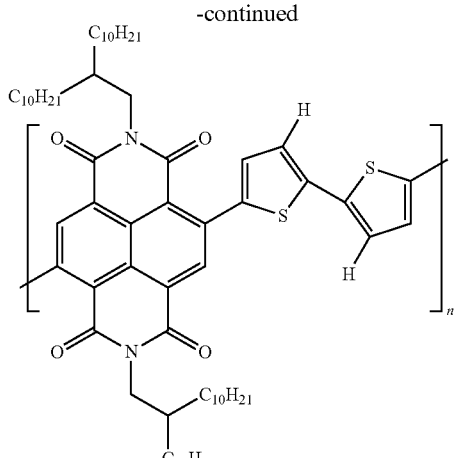

N2200
mobility 0.5 cm²V⁻¹ s⁻¹ (OFET)
5.3% (as acceptor)

In the above donor-acceptor conjugated polymers, PBTff4T-OD, PffT2-FTAZ, PID-ffT4, and N2200-2F exhibited a power conversion efficiency as an acceptor in a range between 6.7 and 10.4%. Donor-acceptor conjugated polymers PBT4T-OD, PT2-FTAZ, PID-T4, PDPP-T4 and N2200 exhibited a power conversion efficiency as an acceptor in a range between 2.6 and 5.3%. N2200-2F and N2200 have an electron hole mobility of 0.3 cm²/Vs and 0.5 cm²/Vs, respectively.

In a further embodiment, the present subject matter provides a formulation comprising an organic solvent, a fullerene and a donor-acceptor conjugated polymer,

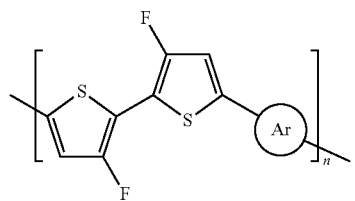

wherein Ar is an aromatic group independently selected from the group consisting of:

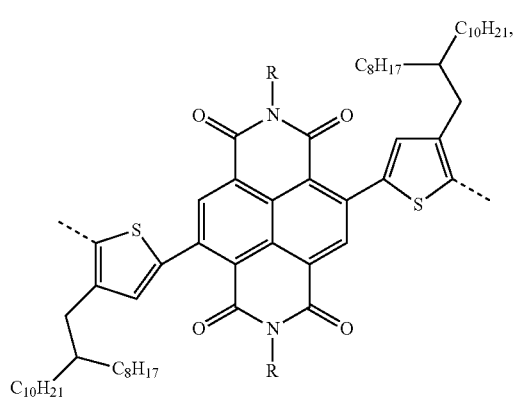

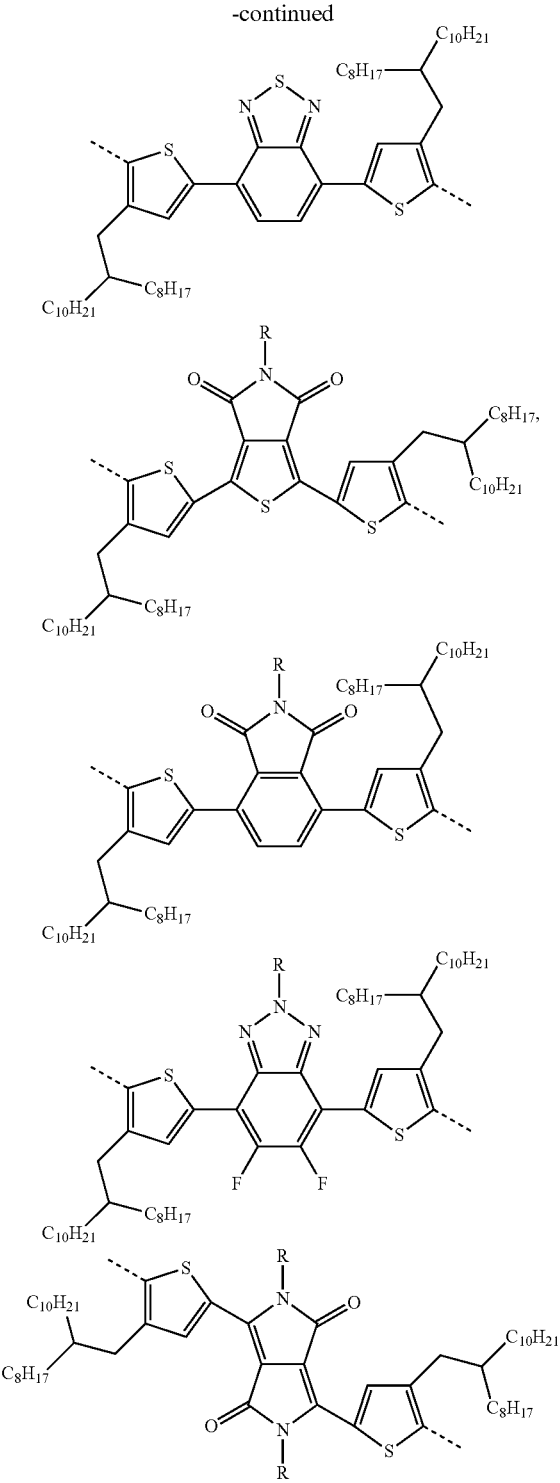

each R is independently selected from the group consisting of straight-chain, branched, and cyclic alkyl with 2-40 C atoms, wherein one or more non-adjacent C atoms are optionally replaced by —O—, —S—, —C(O)—, —C(O)—O—, —O—C(O)—, —O—C(O)—O—, —CR⁰=CR⁰⁰—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein R⁰ and R⁰⁰ are independently a straight-chain, branched, or cyclic alkyl group.
In a further embodiment, the fullerene useful herein can be selected from the group consisting of:
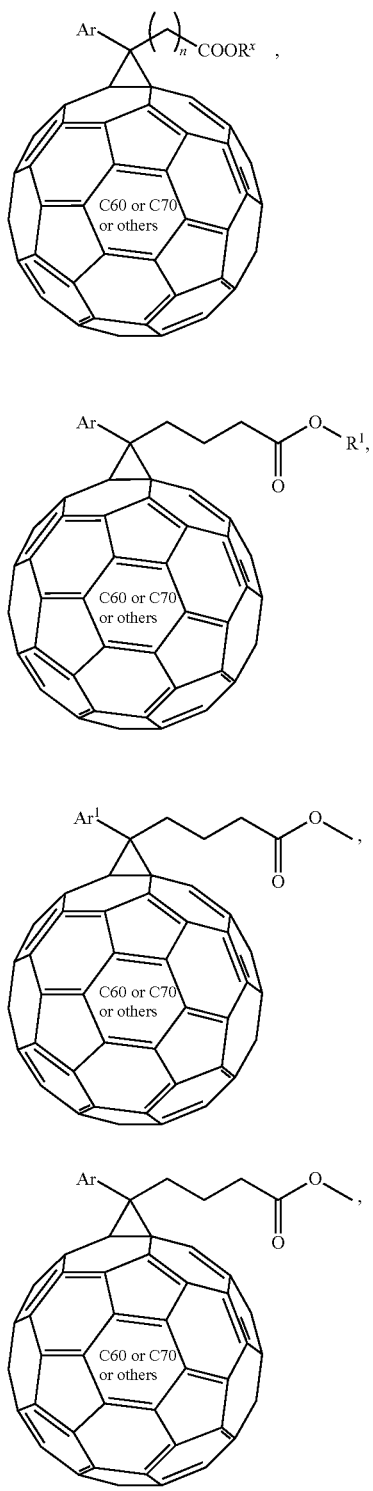
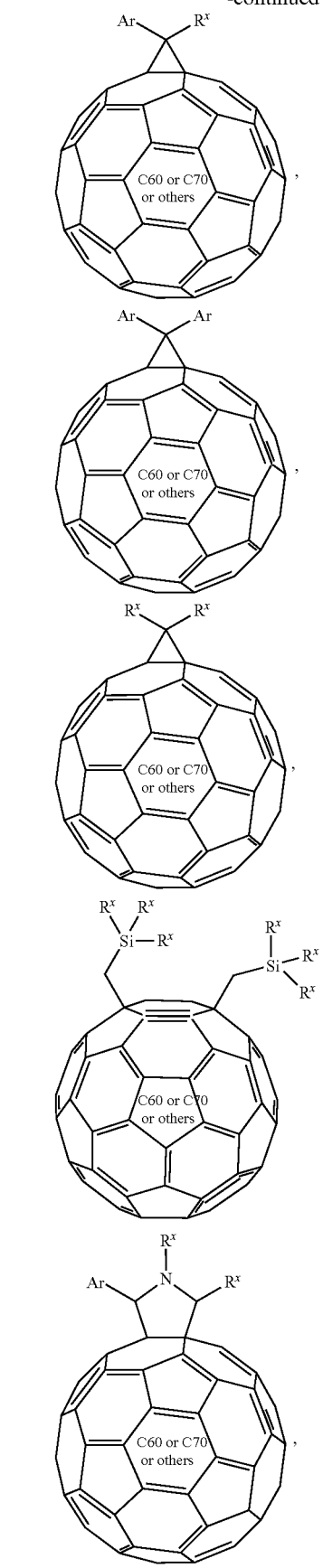

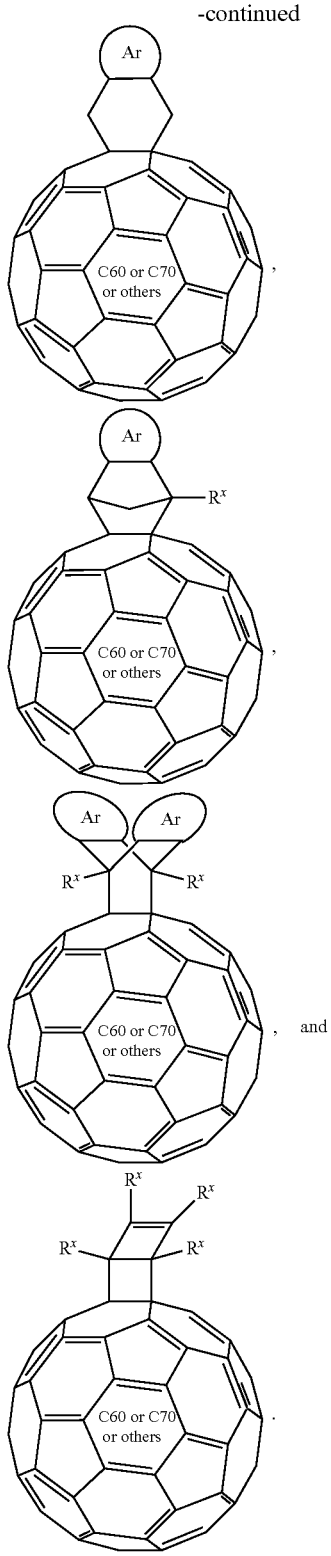

, and

.

wherein each n=1, 2, 4, 5, or 6;

each Ar is independently selected from the group consisting of monocyclic, bicyclic, and polycyclic arylene, and monocyclic, bicyclic, and polycyclic heteroarylene, wherein each Ar may contain one to five of said arylene or heteroarylene each of which may be fused or linked;

each $R^x$ is independently selected from the group consisting of Ar, straight-chain, branched, and cyclic alkyl with 2-40 C atoms, wherein one or more non-adjacent C atoms are optionally replaced by —O—, —S—, —C(O)—, —C(O—)—O—, —O—C(O)—, —O—C(O)—O—, —CR$^O$=CR$^{OO}$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein $R^O$ and $R^{OO}$ are independently a straight-chain, branched, or cyclic alkyl group;

each $R^1$ is independently selected from the group consisting of straight-chain, branched, and cyclic alkyl with 2-40 C atoms, wherein one or more non-adjacent C atoms are optionally replaced by —O—, —S—, —C(O)—, —C(O—)—O—, —O—C(O)—, —O—C(O)—O—, —CR$^O$=CR$^{OO}$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein the number of carbon that $R^1$ contains is larger than 1, wherein $R^O$ and $R^{OO}$ are independently a straight-chain, branched, or cyclic alkyl group;

each $Ar^1$ is independently selected from the group consisting of monocyclic, bicyclic and polycyclic heteroaryl groups, wherein each $Ar^1$ may contain one to five of said heteroaryl groups each of which may be fused or linked;

each $Ar^2$ is independently selected from aryl groups containing more than 6 atoms excluding H; and wherein the fullerene ball represents a fullerene selected from the group consisting of C60, C70, C84, and other fullerenes.

In one embodiment, the fullerene is substituted by one or more functional groups selected from the group consisting of:

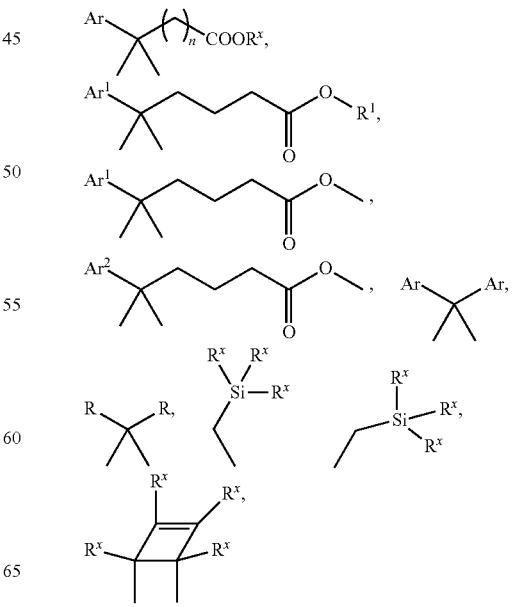

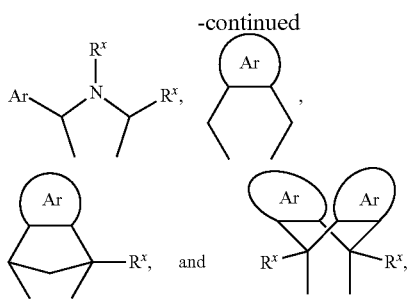

wherein each n=1-6;

each Ar is independently selected from the group consisting of monocyclic, bicyclic, and polycyclic arylene, and monocyclic, bicyclic, and polycyclic heteroarylene, or may contain one to five such groups, either fused or linked;

each $R^x$ is independently selected from the group consisting of Ar, straight-chain, branched, and cyclic alkyl with 2-40 C atoms, wherein one or more non-adjacent C atoms are optionally replaced by —O—, —S—, —C(O)—, —C(O—)—O—, —O—C(O)—, —O—C(O)—O—, —$CR^o$=$CR^{oo}$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein $R^o$ and $R^{oo}$ are independently a straight-chain, branched, or cyclic alkyl group;

each $R^1$ is independently selected from the group consisting of straight-chain, branched, and cyclic alkyl with 2-40 C atoms, wherein one or more non-adjacent C atoms are optionally replaced by —O—, —S—, —C(O)—, —C(O—)—O—, —O—C(O)—, —O—C(O)—O—, —$CR^o$=$CR^{oo}$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein the number of carbon that $R^1$ contains is larger than 1, wherein $R^o$ and $R^{oo}$ are independently a straight-chain, branched, or cyclic alkyl group;

each R is independently selected from the group consisting of straight-chain, branched, and cyclic alkyl with 2-40 C atoms, wherein one or more non-adjacent C atoms are optionally replaced by —O—, —S—, —C(O)—, —C(O—)—O—, —O—C(O)—, —O—C(O)—O—, —$CR^o$=$CR^{oo}$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein $R^o$ and $R^{oo}$ are independently a straight-chain, branched, or cyclic alkyl group;

each $Ar^1$ is independently selected from the group consisting of monocyclic, bicyclic and polycyclic heteroaryl groups, wherein each $Ar^1$ may contain one to five of said heteroaryl groups each of which may be fused or linked;

each $Ar^2$ is independently selected from aryl groups containing more than 6 atoms excluding H; and wherein the fullerene ball represents a fullerene selected from the group consisting of C60, C70, C84, and other fullerenes.

In some embodiments, the formulation is further characterized in that the fullerene is selected from the group consisting of:

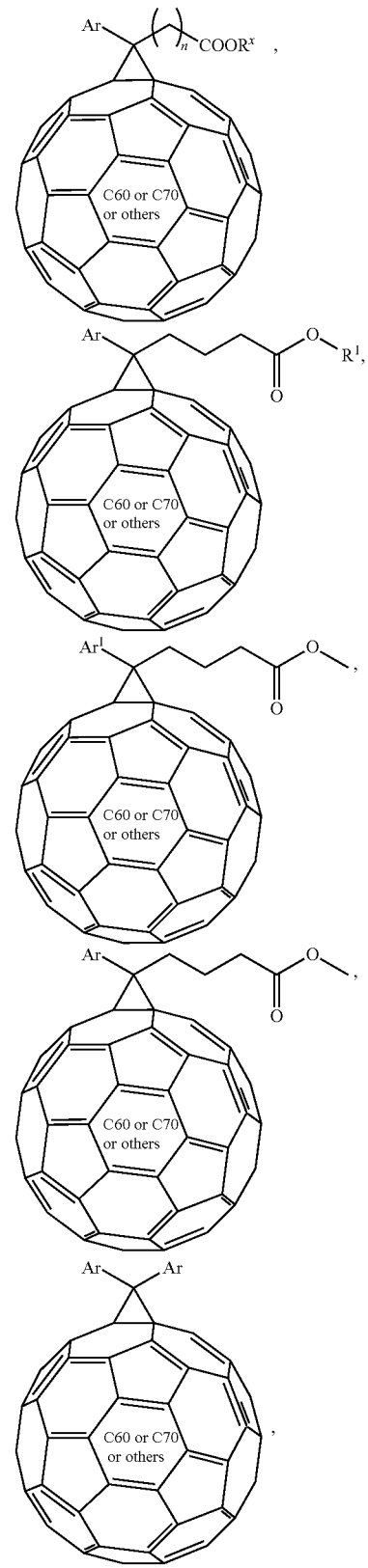

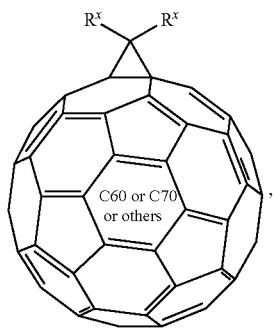,

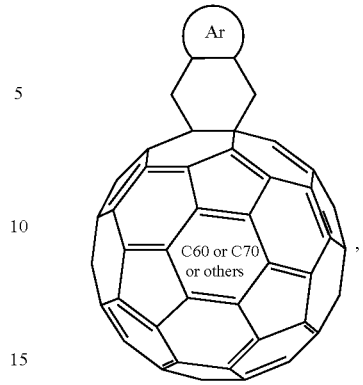,

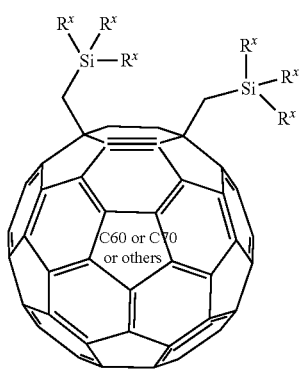,

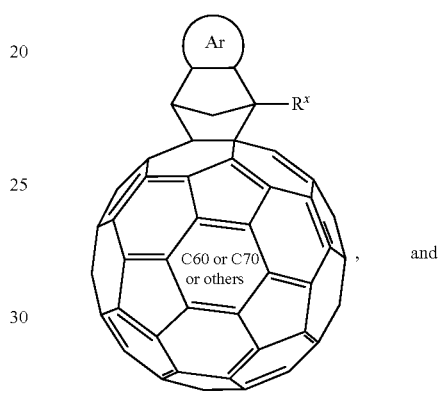,

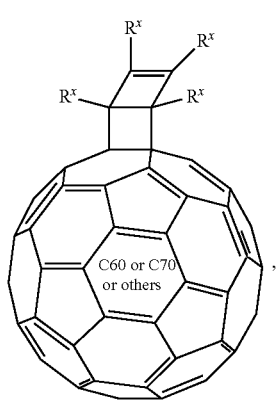,

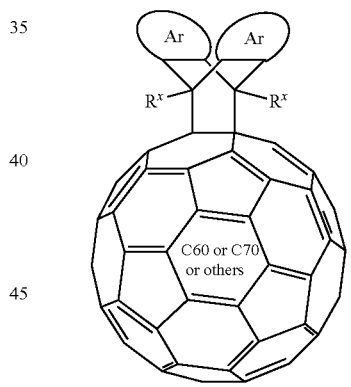, and

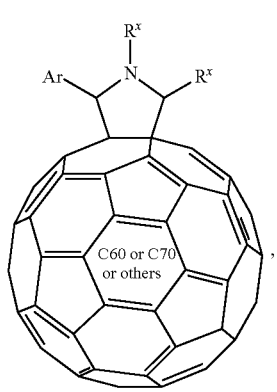, wherein each R is independently selected from the group consisting of straight-chain, branched, and cyclic alkyl with 2-40 C atoms, wherein one or more non-adjacent C atoms are optionally replaced by —O—, —S—, —C(O)—, —C(O)—O—, —O—C(O)—, —O—C(O)—O—, —CR$^0$=CR$^{00}$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein R$^0$ and R$^{00}$ are independently a straight-chain, branched, or cyclic alkyl group.

In some embodiments, the formulation is further characterized in that the fullerene is selected from the group consisting of:

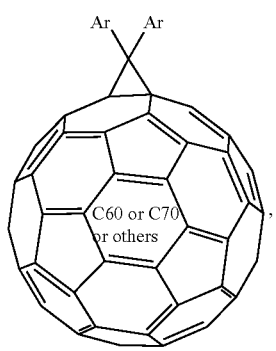
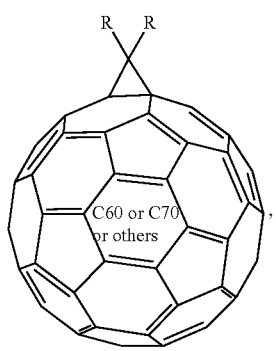
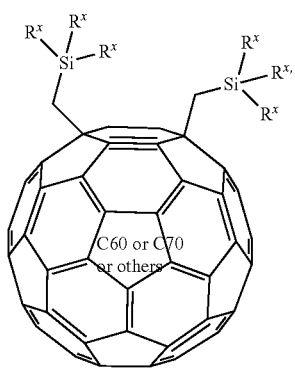
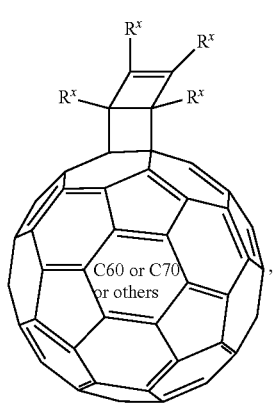
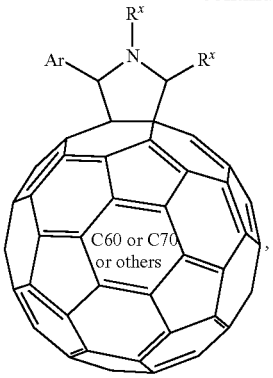
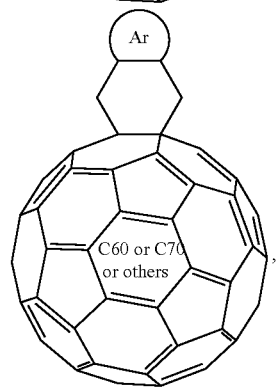
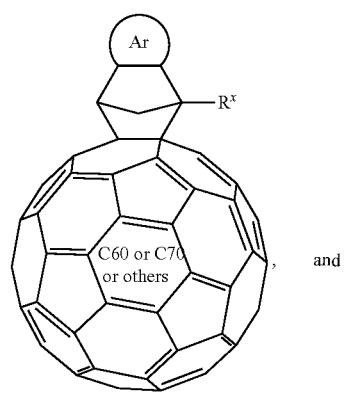
and
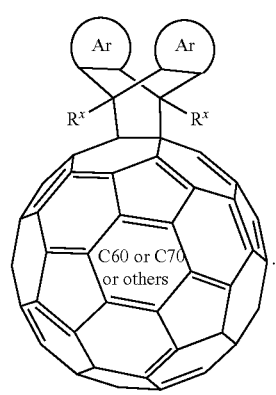
In some embodiments, the formulation is further characterized in that the fullerene is selected from the group consisting of:

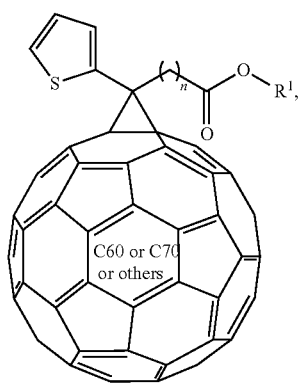

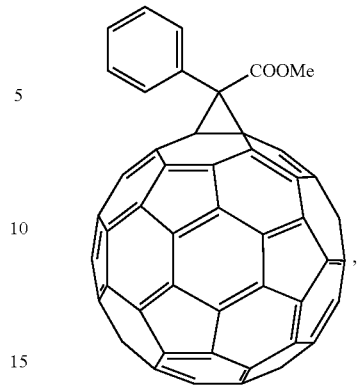

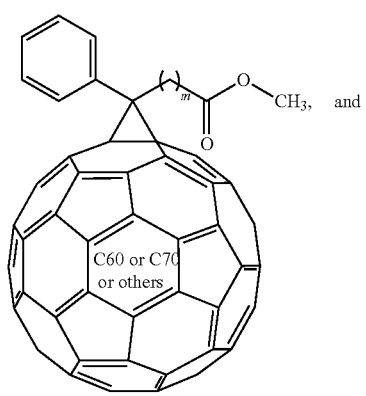

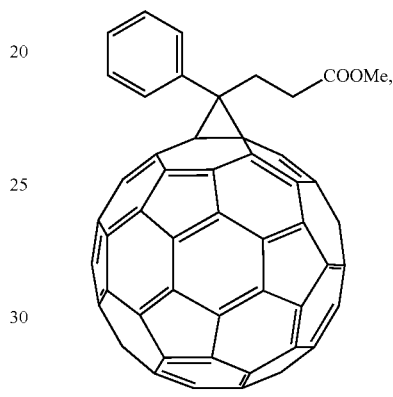

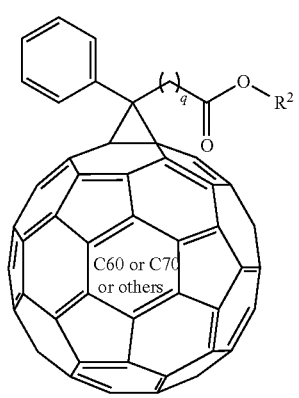

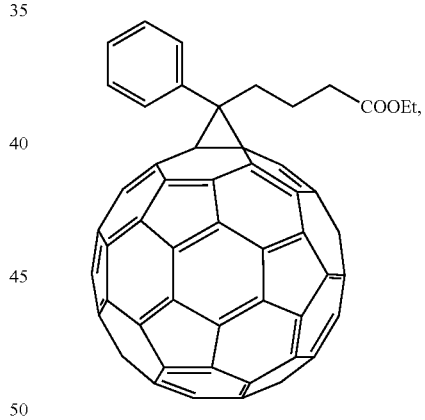

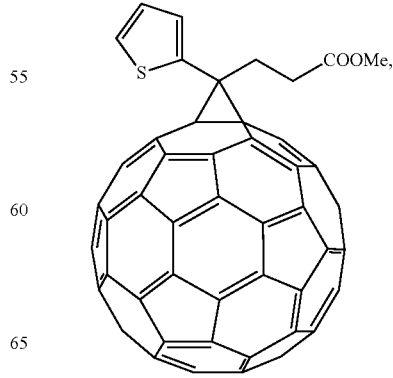

wherein each n=1-6;
each m=1, 2, 4, 5, or 6;
each q=1-6;
each $R^1$ and $R^2$ is independently selected from the group consisting of C1-4 straight and branched chain alkyl groups; and
wherein the fullerene ball represents a fullerene from the group consisting of C60, C70, C84, and other fullerenes.

In some embodiments, the formulation is further characterized in that the fullerene is selected from the group consisting of:

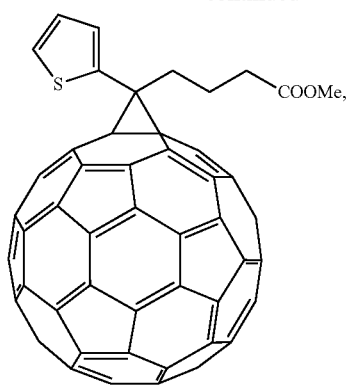
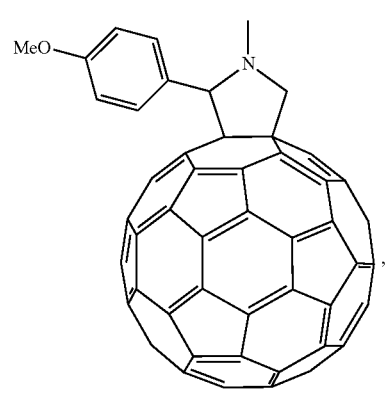
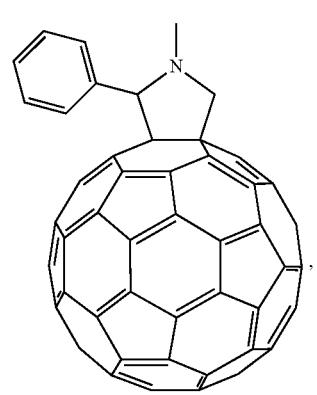
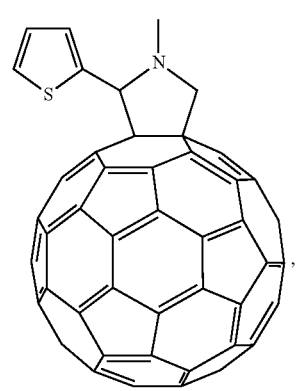
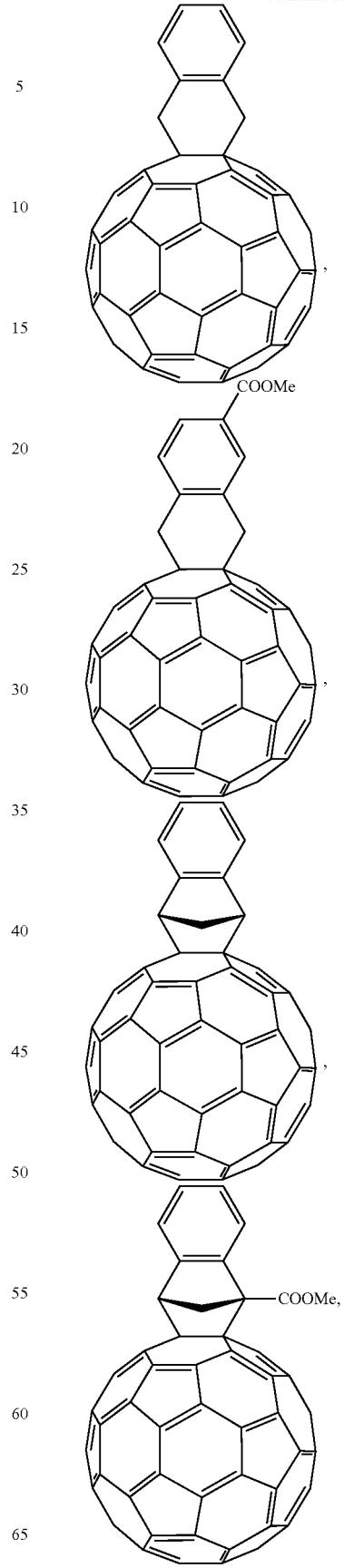

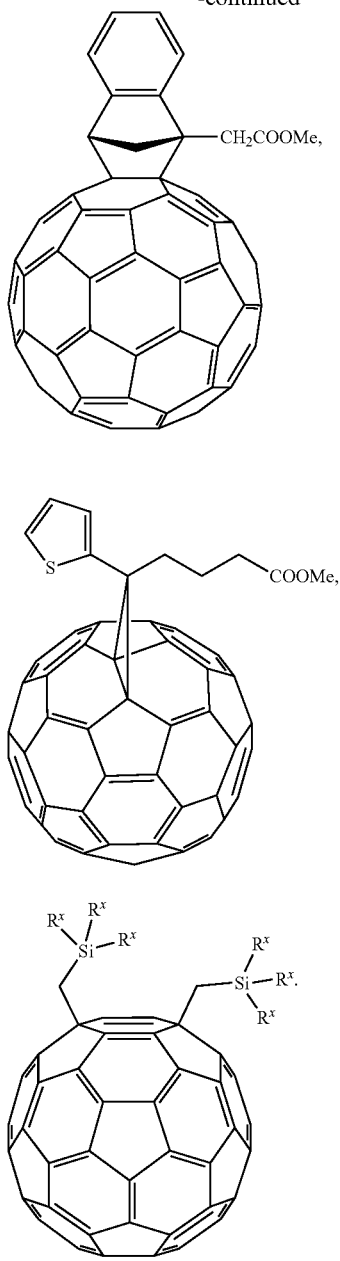

In an exemplary embodiment, an organic electronic (OE) device comprises a coating or printing ink containing the formulation. Another exemplary embodiment is further characterized in that the OE device is an organic field effect transistor (OFET) device. Another exemplary embodiment is further characterized in that the OE device is an organic photo voltaic (OPV) device.

In an another embodiment of the present subject matter, a thin film is provided comprising a donor-acceptor conjugated polymer and a fullerene, wherein a solution of the donor-acceptor conjugated polymer exhibits a peak optical absorption spectrum red shift of at least 100 nm when the donor-acceptor conjugated polymer solution is cooled from 140° C. to room temperature, and wherein the donor-acceptor conjugated polymer comprises one or more repeating units of the following formula:

wherein Ar is an aromatic group independently selected from the group consisting of:

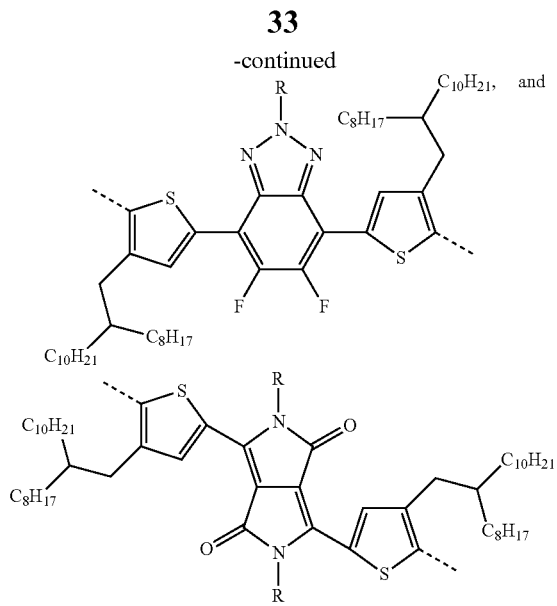

each R is independently selected from the group consisting of straight-chain, branched, and cyclic alkyl with 2-40 C atoms, wherein one or more non-adjacent C atoms are optionally replaced by —O—, —S—, —C(O)—, —C(O)—O—, —O—C(O)—, —O—C(O)—O—, —CR$^o$═CR$^{oo}$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein R$^o$ and R$^{oo}$ are independently a straight-chain, branched, or cyclic alkyl group.

Formulations of the present teachings can exhibit semiconductor behavior such as optimized light absorption/charge separation in a photo voltaic device; charge transport/recombination/light emission in a light-emitting device; and/or high carrier mobility and/or good current modulation characteristics in a field-effect device. In addition, the present formulations can possess certain processing advantages such as solution-processability and/or good stability (e.g., air stability) in ambient conditions. The formulations of the present teachings can be used to prepare either p-type (donor or hole-transporting), n-type (acceptor or electron-transporting), or ambipolar semiconductor materials, which in turn can be used to fabricate various organic or hybrid optoelectronic articles, structures and devices, including organic photo voltaic devices and organic light-emitting transistors.

EXAMPLES

Example 1—Synthesis of Monomers

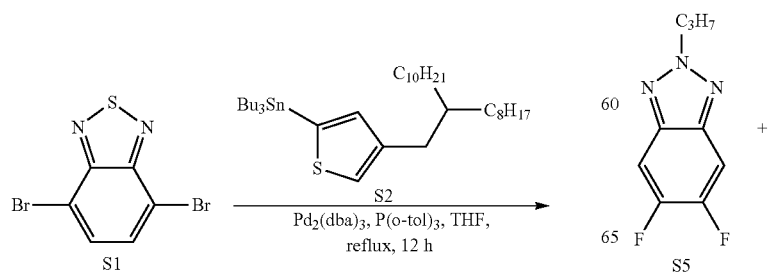

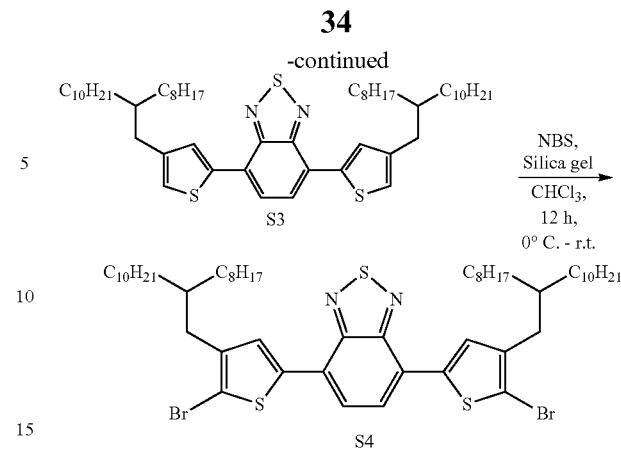

Step 1: Preparation of 4,7-bis(4-(2-octyldodecyl)-2-thienyl)-2,1,3-benzothiadiazole (S3)

A solution of 3-(2-octyldodecyl)thiophene (5.00 g, 13.7 mmol) in 50 mL THF was cooled to −78° C. under $N_2$. Lithium diisopropylamide (2 M, 8.3 mL, 16.6 mmol) was added dropwise and the mixture was stirred at −78° C. for 1 h and then return to 0° C. and stirred for additional 1 h. Then the mixture was cooled to −78° C. and tri-n-butyltin chloride (6.50 g, 20 mmol) was added in one portion. The reaction mixture was return to r.t. and stirred overnight. A solution of KF in water was added and the organic phase was washed with water for three times, then dried with $Na_2SO_4$. The solvent was evaporated to get the crude product as yellow oil, which is directly used without further purification. A mixture of 2-(tri-n-butylstannyl)-4-(2-octyldodecyl)thiophene (1.96 g, 3 mmol), 4,7-dibromo-2,1,3-benzothiadiazole (305 mg, 1 mmol), $Pd_2(dba)_3$ (11 mg, 0.02 mmol) and P(o-tol)$_3$ (24 mg, 0.08 mmol) in 10 mL THF was refluxed overnight under $N_2$. The reaction mixture was then cooled to r.t. and the solvent was evaporated. The residue was purified by flash column chromatography (eluent: n-hexane) to get the product as yellow solid (650 mg, 73%).

Step 2: Preparation of 4,7-bis(5-bromo-4-(2-octyldodecyl)-2-thienyl)-2,1,3-benzothiadiazole (S4)

N-Bromosuccinimide (540 mg, 3.00 mmol) was added to a mixture of S3 (1.22 g, 1.36 mmol) and silica gel (20 mg) in 20 mL chloroform at 0° C. The reaction mixture was warmed to r.t. and stirred overnight. After washed with water, the organic phase was dried with $Na_2SO_4$ and the solvent was evaporated. The residue was purified with flash column chromatography (eluent: n-hexane) to get the product as orange solid (1.42 g, 99%).

-continued

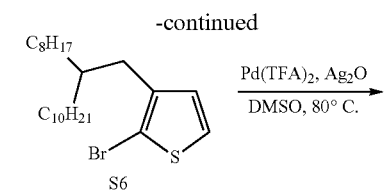

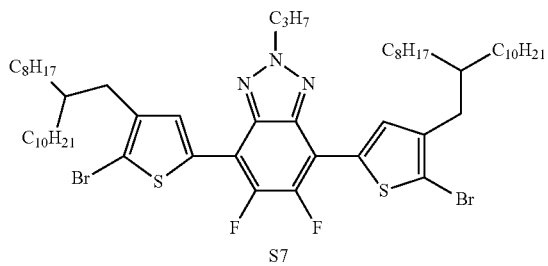

Step 3: Preparation of 4,7-bis(5-bromo-4-(2-octyl-dodecyl) thiophen-2-yl)-5,6-difluoro-2-propyl-2H-benzo[d][1,2,3]triazole (S7)

To a 50 mL tube were added S5 (197 mg, 1 mmol, S6 (1.33 g, 3 mmol), Pd(TFA)$_2$ (16.6 mg, 0.05 mmol), Ag$_2$O (927 mg, 4 mmol) and DMSO. And then heated at 80° C. with stirring for 8 h. After cooled to room temperature, the reaction mixture was filtered, diluted with chloroform and washed with brine. The organic layer was dried over Na$_2$SO$_4$, filtered and concentrated. Then the residue was purified with silica gel chromatography to provide pure product (720 mg, 63.7% yield).

Example 2—Polymer Synthesis

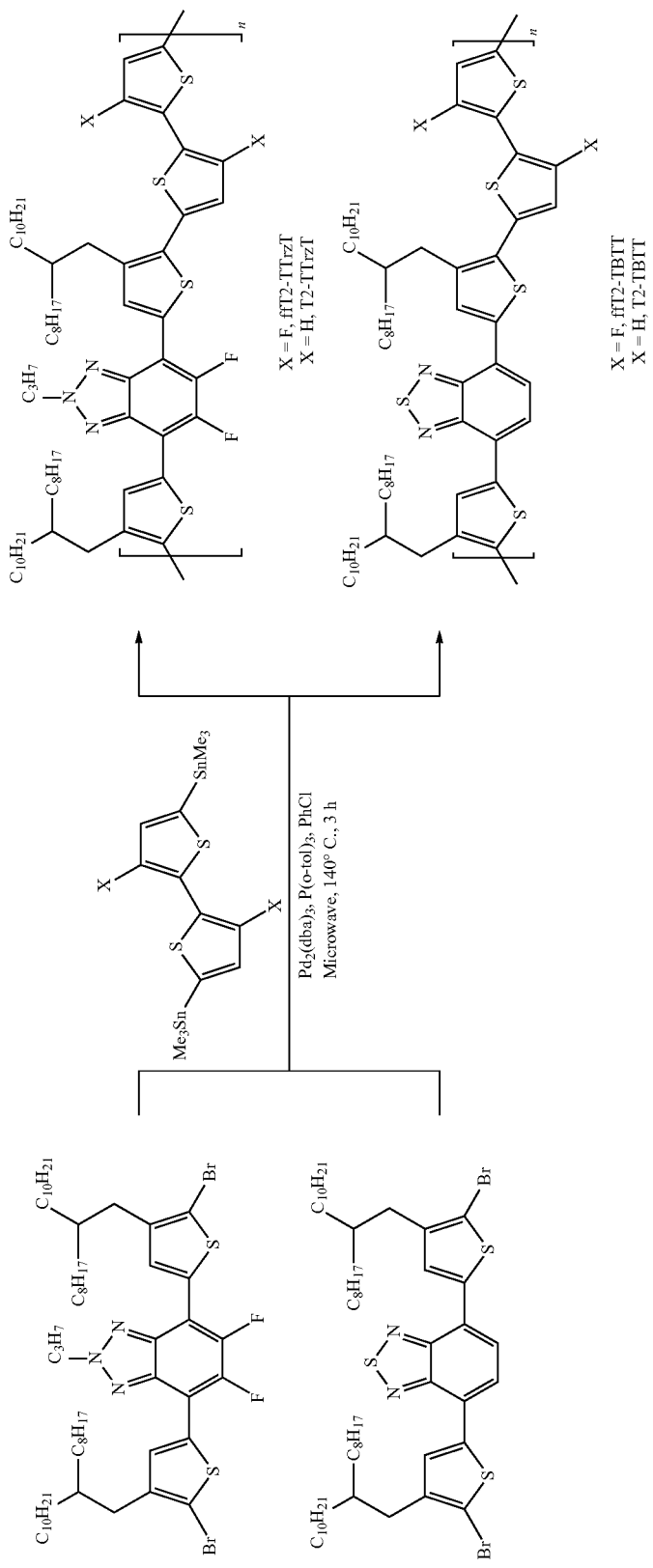

The ffT2-TBTT can be synthesized by either microwave reaction or conventional reaction. To a mixture of monomer S4 (96.5 mg, 0.095 mmol), (3,3'-difluoro-[2,2'-bithiophene]-5,5'-diyl)bis(trimethylstannane) (50.2 mg, 0.095 mmol), Pd$_2$(dba)$_3$ (1.1 mg, 0.002 mmol) and P(o-tol)$_3$ (2.4 mg, 0.008 mmol) was added 1.6 mL of chlorobenzene in a glove box protected with N$_2$. The reaction mixture was then sealed and heated at 145° C. for 2 days (or at 160° C. for 30 min for microwave reaction). The mixture was cooled to r.t. and 10 mL toluene was added before precipitated with methanol. The solid was collected by filtration, and purified by Soxhlet extraction (CH$_2$Cl$_2$, CHCl$_3$, and chlorobenzene) and repetitive precipitation. The solvent was evaporated and the residue was dissolved in chlorobenzene and precipitated with methanol. The solid was collected by filtration and dried in vacuo to get the polymer as dark green solid (89 mg, 88%). 1H NMR (400 MHz, CDCl3) δ 8.04 (s, 2H), 7.90 (s, 2H), 7.08 (s, 2H), 2.89 (d, J=6.6 Hz, 4H), 1.91 (s, 2H), 1.51-1.23 (m, 64H), 0.92 (t, J=6.8 Hz, 12H) . . . Elem. Anal. Calcd for C$_{62}$H$_{88}$F$_2$N$_2$S$_5$: C, 70.27; H, 8.37; F, 3.59; N, 2.64; S, 15.13. Found: C, 70.33; H, 8.16; F, 3.70; N, 2.72; S, 14.91. GPC Number-averaged molecular weight (M$_n$): 25 kDa; weight-averaged molecular weight (M$_w$): 37 kDa.

The T2-TBTT can be synthesized by either microwave reaction or conventional reaction. To a mixture of monomer S4 (96.5 mg, 0.095 mmol), [2,2'-bithiophene]-5,5'-diyl)bis(trimethylstannane) (46.8 mg, 0.095 mmol), Pd$_2$(dba)$_3$ (1.1 mg, 0.002 mmol) and P(o-tol)$_3$ (2.4 mg, 0.008 mmol) was added 1.6 mL of chlorobenzene in a glove box protected with N$_2$. The reaction mixture was then sealed and heated at 145° C. for 2 days (or at 160° C. for 30 min for microwave reaction). The mixture was cooled to r.t. and 10 mL toluene was added before precipitated with methanol. The solid was collected by filtration, and purified by Soxhlet extraction (CH$_2$Cl$_2$, CHCl$_3$, and chlorobenzene) and repetitive precipitation. The solvent was evaporated and the residue was dissolved in chlorobenzene and precipitated with methanol. The solid was collected by filtration and dried in vacuo to get the polymer as dark green solid (81 mg, 80%). $^1$H NMR (400 MHz, CDCl$_3$) δ8.05 (s, 2H), 7.89 (s, 2H), 7.25 (d, J=3.8 Hz, 2H), 7.22 (d, J=3.7 Hz, 2H) 2.90 (d, J=6.9 Hz, 4H), 1.92 (s, 2H), 1.51-1.25 (m, 64H), 0.92 (t, J=6.6 Hz, 12H). GPC Number-averaged molecular weight (M$_n$): 18 kDa; weight-averaged molecular weight (M$_w$): 30 kDa.

The ffT2-TTrzT can be synthesized by either microwave reaction or conventional reaction. To a mixture of monomer S7 (107.4 mg, 0.095 mmol), [2,2'-bithiophene]-5,5'-diyl)bis(trimethylstannane) (46.8 mg, 0.095 mmol), Pd$_2$ (dba)$_3$ (1.1 mg, 0.002 mmol) and P (o-tol)$_3$ (2.4 mg, 0.008 mmol) was added 1.6 mL of chlorobenzene in a glove box protected with N$_2$. The reaction mixture was then sealed and heated at 145° C. for 2 days (or at 160° C. for 30 min for microwave reaction). The mixture was cooled to r.t. and 10 mL toluene was added before precipitated with methanol. The solid was collected by filtration, and purified by Soxhlet extraction (CH$_2$Cl$_2$, CHCl$_3$, and chlorobenzene) and repetitive precipitation. The solvent was evaporated and the residue was dissolved in chlorobenzene and precipitated with methanol. The solid was collected by filtration and dried in vacuo to get the polymer as dark green solid (75 mg, 70%). $^1$H NMR (400 MHz, CDCl$_3$) δ8.18 (s, 2H), 7.09 (s, 2H), 4.83 (s, 2H), 2.91 (d, J=7.3 Hz, 4H), 2.31 (dd, J=14.5, 7.2 Hz, 2H), 1.91 (s, 2H), 1.52-1.27 (m, 64H), 1.17 (t, J=7.4 Hz, 3H), 0.92 (dd, J=6.9, 5.4 Hz, 12H). Anal. Calcd for C$_{65}$H$_{93}$F$_4$N$_3$S$_4$: C, 69.66; H, 8.36; N, 3.75. Found C, 69.29; H, 8.28; N, 3.90. Mn: 41.5 KDa, Mw: 76.5 KDa; PDI=1.84.

The T2-TTrzT can be synthesized by either microwave reaction or conventional reaction. To a mixture of monomer S4 (107.4 mg, 0.095 mmol), [2,2'-bithiophene]-5,5'-diyl)bis (trimethylstannane) (46.8 mg, 0.095 mmol), Pd$_2$(dba)$_3$ (1.1 mg, 0.002 mmol) and P(o-tol)$_3$ (2.4 mg, 0.008 mmol) was added 1.6 mL of chlorobenzene in a glove box protected with N$_2$. The reaction mixture was then sealed and heated at 145° C. for 2 days (or at 160° C. for 30 min for microwave reaction). The mixture was cooled to r.t. and 10 mL toluene was added before precipitated with methanol. The solid was collected by filtration, and purified by Soxhlet extraction (CH$_2$Cl$_2$, CHCl$_3$, and chlorobenzene) and repetitive precipitation. The solvent was evaporated and the residue was dissolved in chlorobenzene and precipitated with methanol. The solid was collected by filtration and dried in vacuo to get the polymer as dark green solid (75 mg, 72%). $^1$H NMR (400 MHz, CDCl$_3$) δ8.19 (s, 2H), 7.26 (d, J=3.7 Hz, 2H), 7.23 (d, J=3.8 Hz, 2H), 4.83 (s, 2H), 2.92 (d, J=6.5 Hz, 4H), 2.31 (dd, J=14.5, 7.2 Hz, 2H), 1.92 (s, 2H), 1.55-1.26 (m, 64H), 1.18 (t, J=7.4 Hz, 3H), 0.92 (dt, J=7.0, 3.4 Hz, 12H). Anal. Calcd for C$_{65}$H$_{95}$F$_2$N$_3$S$_4$: C, 71.97; H, 8.83; N, 3.87. Found C, 70.58; H, 8.24; N, 4.48. Mn: 80.9 KDa; Mw: 150.8 KDa; PDI=1.86.

Example 3—Characterization of Polymers

Example 3a: Optical Properties

Optical absorption measurements of polymers from Example 2 were carried out using a Cary UV-vis spectrometer on DCB solution of the polymer. The onset of the absorption is used to estimate the polymer bandgap. The optical absorption spectrum is shown in FIG. 1.

Example 3b: Electronic Properties

Cyclic voltammetry was performed in an electrolyte solution of 0.1 M tetrabutylammonium hexafluorophosphate, both working and counter electrodes were platinum electrode. Ag/AgCl electrode was used as the reference electrode; the Fc/Fc+ redox couple was used as an external standard (shown in FIG. 2a-d).

Example 4—Device Fabrication

Example 4a: Photo Voltaic Cell Fabrication and Measurements

Pre-patterned ITO-coated glass with a sheet resistance of ~15 Ω/square was used as the substrate. It was cleaned by sequential sonications in soap DI water, DI water, acetone, and isopropanol. After UV/ozone treatment for 60 min, a ZnO electron transport layer was prepared by spin-coating at 5000 rpm from a ZnO precursor solution (diethyl zinc). Active layer solutions were prepared in CB/DCB or CB/DCB/DIO with various ratios (polymer concentration: 7-12 mg/mL). To completely dissolve the polymer, the active layer solution should be stirred on hot plate at 100-120° C. for at least 3 hours. Active layers were spin-coated from warm solutions in a N$_2$ glove box at 600-850 rpm to obtain thicknesses of ~250-350 nm. The polymer/fullerene films were then annealed at 80° C. for 5 min before being transferred to the vacuum chamber of a thermal evaporator inside the same glove box. At a vacuum level of 3×10$^{-6}$ Torr, a thin layer (20 nm) of MoO$_3$ or V$_2$O$_5$ was deposited as the anode interlayer, followed by deposition of 100 nm of Al as the top electrode. All cells were encapsulated using epoxy inside the globebox. Device J-V characteristics was measured under AM1.5 G (100 mW/cm$^2$) using a Newport solar simulator. The light intensity was calibrated using a standard Si diode (with KG5 filter, purchased from PV Measurement) to bring spectral mismatch to unity. J-V characteristics were recorded using a Keithley 236 source meter unit. Typical cells have devices area of about 5.9 mm$^2$, which is defined by a metal mask with an aperture aligned with the device area. EQEs were characterized using a Newport EQE system equipped with a standard Si diode. Monochromatic light was generated from a Newport 300 W lamp source. The Voc, Jsc, FF and PCE of OPV devices in the present teaching are summarized in the following table.

TABLE 1

PSC performance of ffT2-TBTT and T2-TBTT with PC$_{71}$BM

| Polymer: PC$_{71}$BM | V$_{oc}$ (V) | J$_{sc}$ (mA/cm$^2$) | FF | PCE$_{max}$ (%) | PCE$_{ave}$ (%) |
|---|---|---|---|---|---|
| T2-TBTT | 0.67 | 6.0 | 0.49 | 2.0 | 2.0 |
| T2-TTrzT | 0.73 | 5.3 | 0.55 | 2.8 | 2.1 |
| ffT2-TBTT | 0.77 | 17.7 | 0.70 | 9.5 | 9.0 |
| ffT2-TTrzT | 0.80 | 13.3 | 0.69 | 7.5 | 7.7 |

Example 5

Preparation of (E)-6,6'-bis(5-bromo-4-(2-octyldodecyl)thiophen-2-yl)-1,1'-dioctyl[3,3'-biindolinylidene]-2,2'-dione (S11)

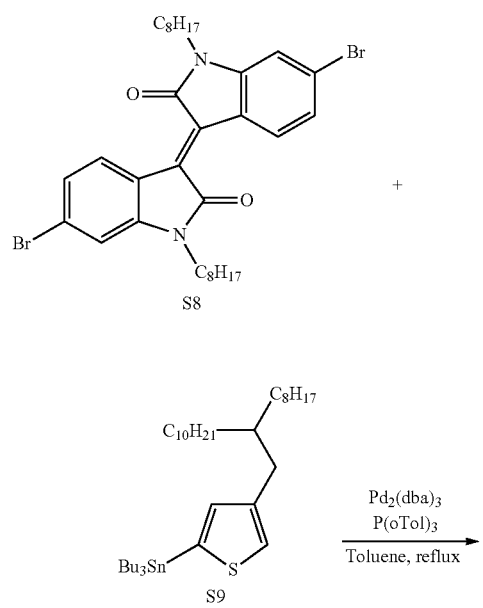

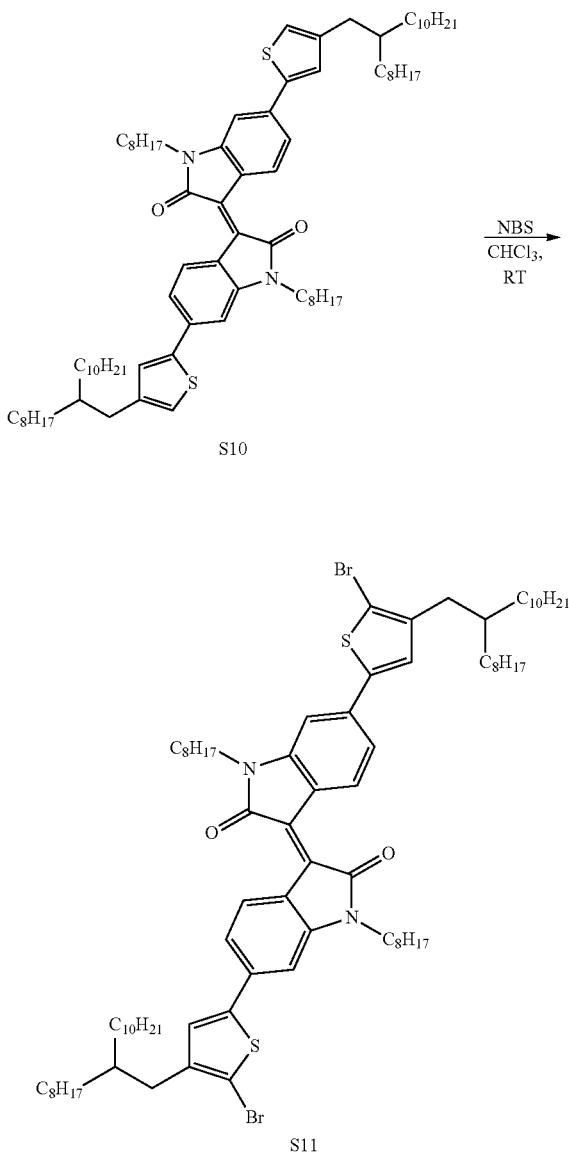

To a solution of S8 (258 mg, 0.4 mmol), Pd$_2$(dba)$_3$ (7 mg, 0.008 mmol) and P(o-tol)$_3$ (10 mg, 0.03 mmol) in 20 mL toluene was added S9 (654 mg, 1.0 mmol) under N$_2$, the reaction was refluxed overnight. After the reaction mixture was cooled to r.t., a solution of KF in water was added and the organic phase was washed with water for three times, then dried with Na$_2$SO$_4$. The solvent was evaporated and the residue was purified by flash column chromatography (eluent: n-hexane/DCM=3:1) to give S10 as a dark solid (368 mg, 76%).

To a solution of S10 (243 mg, 0.2 mmol) in 10 mL CHCl3 was added NBS (71 mg, 0.4 mmol) at 0° C., the reaction was stirred overnight, the mixture was washed with water for three times, then dried with Na$_2$SO$_4$. The solvent was evaporated and the residue was purified by flash column chromatography (eluent: n-hexane/DCM=3:1) to give S11 as a dark solid (250 mg, 80%).

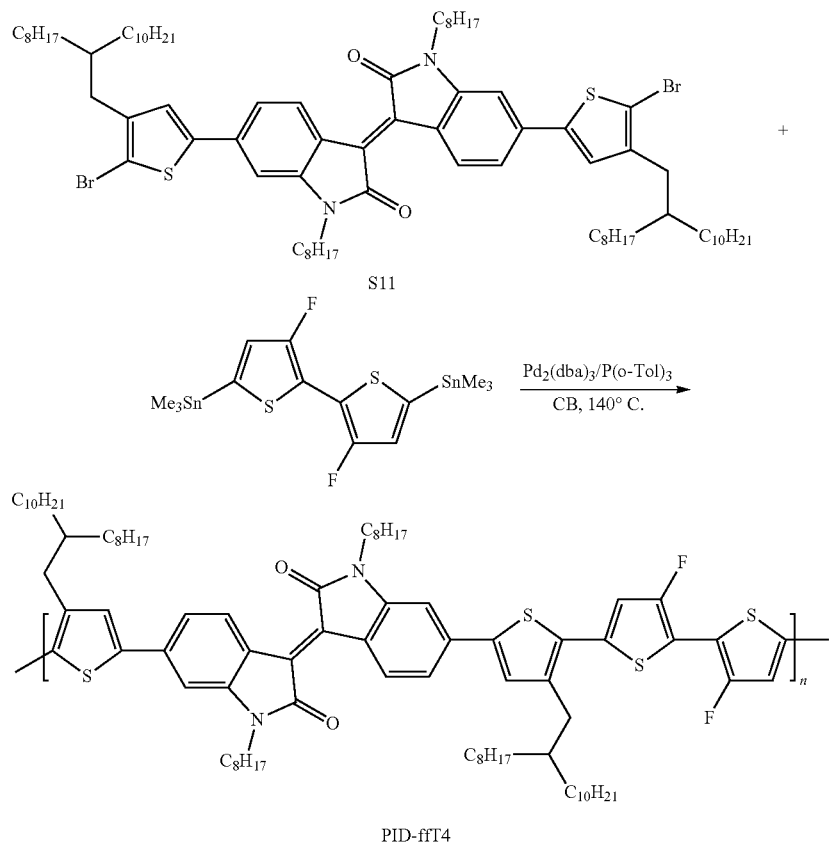

PID-ffT4

For the polymer of PID-ffT4: to a 10 mL of sealed tube were added monomer S11 (27.4 mg, 0.02 mmol), monomer 8 (10.6 mg, 0.02 mmol), tris(dibenzylideneacetone)dipalladium (0.5 mg), tri-o-tolylphosphine (1.0 mg) and CB (0.3 mL) under $N_2$. The mixture was vigorously stirred at 140° C. for 24 h. After cooling to room temperature, the reaction mixture was poured into 100 mL methanol. The precipitate was collected and further purified by Soxhlet extraction with methanol, acetone, chloroform, chlorobenzene successively. The polymer was recovered as a solid from the chlorobenzene fraction to afford the product as a dark green solid (38 mg, 70%). This polymer PID-ffT4 yielded polymer solar cells with 7% efficiency, which is significantly higher than the corresponding polymer without any fluorination.

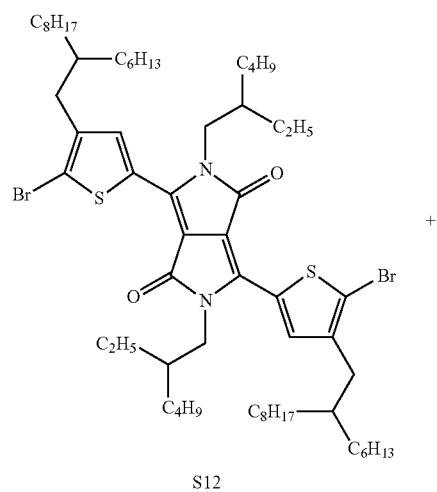

S12

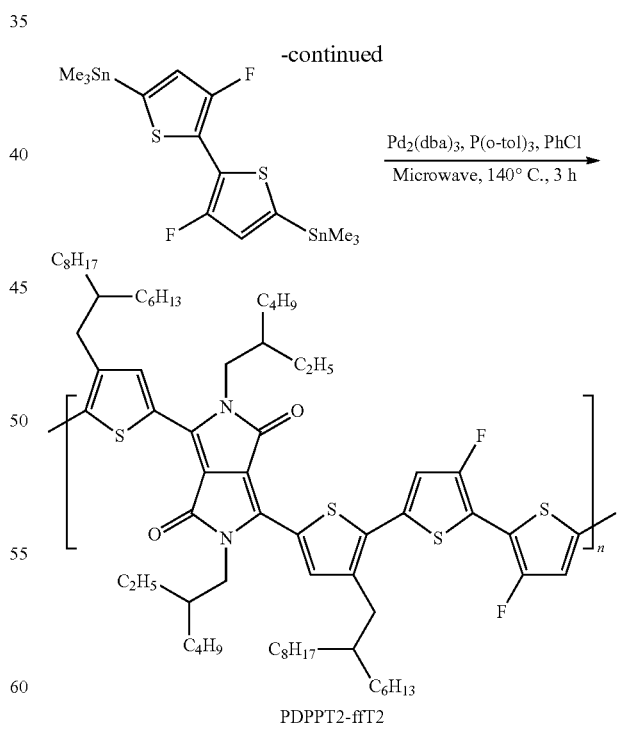

PDPPT2-ffT2

For the polymer of PDPPT2-ffT2: to a 10 mL of sealed tube were added monomer S12 (22.6 mg, 0.02 mmol), monomer 8 (10.6 mg, 0.02 mmol), tris(dibenzylideneacetone)dipalladium (1.0 mg), tri-o-tolylphosphine (2.0 mg)

and CB (0.3 mL) under N$_2$. The mixture was vigorously stirred at 140° C. for 24 h. After cooling to room temperature, the reaction mixture was poured into 100 mL methanol. The precipitate was collected and further purified by Soxhlet extraction with methanol, acetone, chloroform successively. The polymer was recovered as a solid from the chlorobenzene fraction to afford the product as a dark green solid (15 mg, 65%).

which are obvious to those skilled in chemistry, biochemistry, or related fields are intended to be within the scope of the following claims.

We claim:

1. A donor-acceptor conjugated polymer comprising one or more repeating units of the following formula:

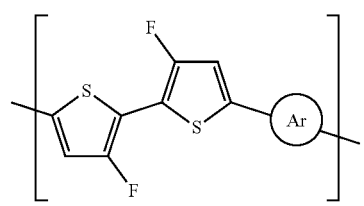

wherein Ar is an aromatic unit selected from the group consisting of:

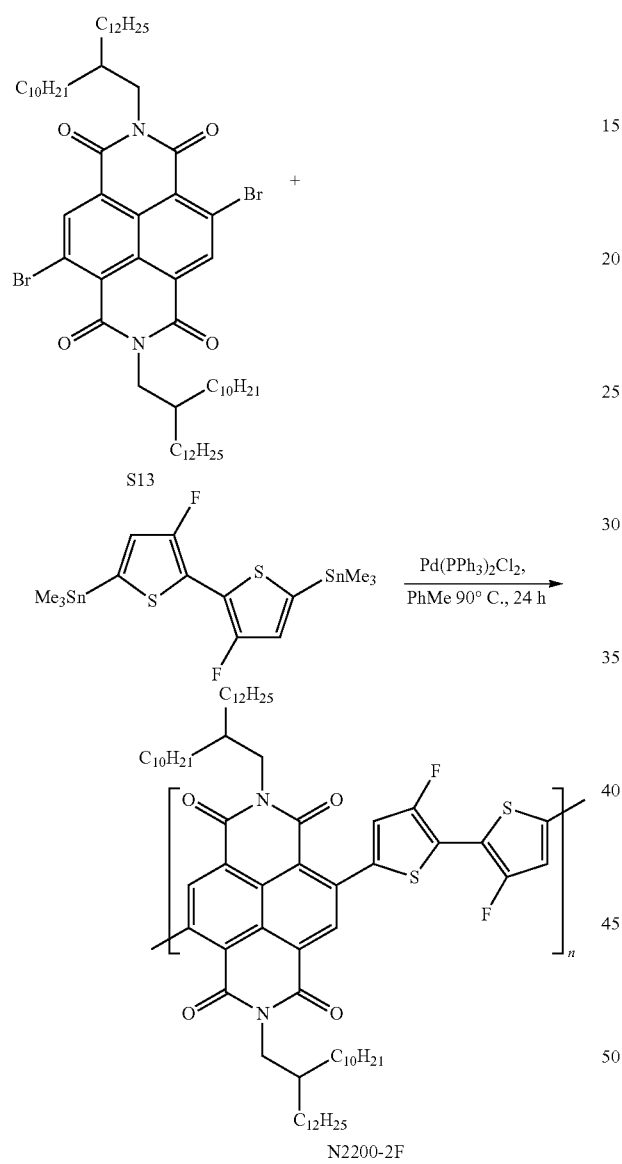

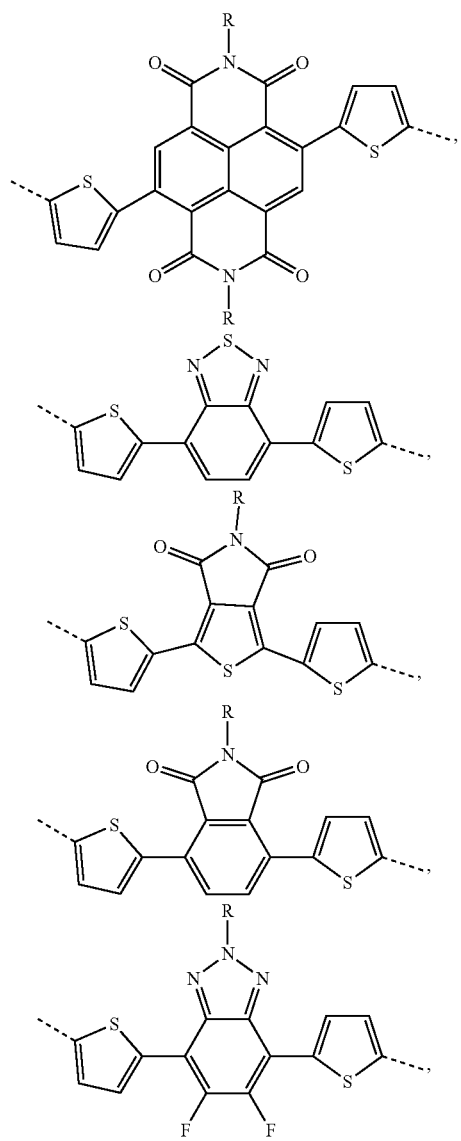

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter

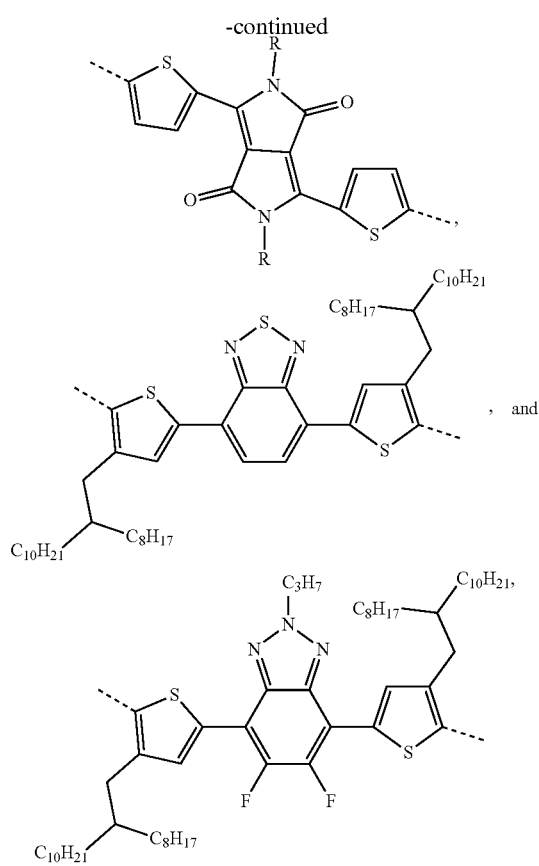

, and

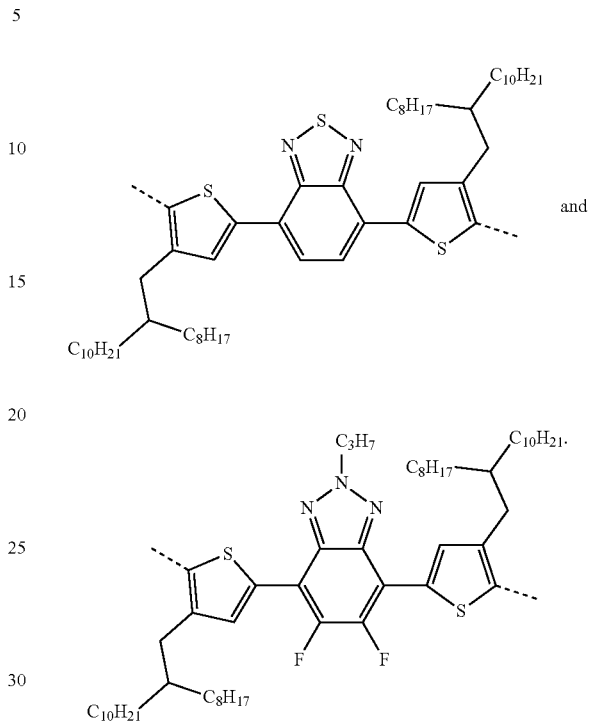

and wherein each R is independently selected from the group consisting of straight-chain, branched, and cyclic alkyl with 2-40 C atoms, wherein one or more non-adjacent C atoms are optionally replaced by —O—, —S—, —C(O)—, —C(O—)—O—, —O—C(O)—, —O—C(O)—O—, —CR°=CR°°—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein R° and R°° are independently a straight-chain, branched, or cyclic alkyl group.

2. The donor-acceptor conjugated polymer of claim 1, wherein the average molecular weight of the conjugated donor-acceptor polymer is in a range from 20,000 to 40,000 gram/mole.

3. The donor-acceptor conjugated polymer of claim 1, wherein a solution of the donor-acceptor conjugated polymer exhibits a peak optical absorption spectrum red shift of at least 100 nm when the donor-acceptor conjugated polymer solution is cooled from 140° C. to room temperature.

4. The donor-acceptor conjugated polymer of claim 1, wherein a solution of the donor-acceptor conjugated polymer exhibits a peak optical absorption spectrum red shift at about 740 nm when the donor-acceptor conjugated polymer solution is cooled from 140° C. to room temperature.

5. The donor-acceptor conjugated polymer of claim 1, further characterized in that the donor-acceptor conjugated polymer has an optical bandgap of 1.65 eV or lower.

6. The donor-acceptor conjugated polymer of claim 1, wherein Ar is selected from a group consisting of:

7. The donor-acceptor conjugated polymer of claim 6, having a power conversion efficiency as an acceptor in a range between 6.7 and 10.4%.

8. The donor-acceptor conjugated polymer of claim 6, wherein a power conversion efficiency of the donor-acceptor conjugated polymer with phenyl-$C_{71}$-butyric-acid-methyl-ester ($PC_{71}BM$) is in a range between 2.0 and 9.0%.

9. The donor-acceptor conjugated polymer of claim 6, wherein a fill factor of the donor-acceptor conjugated polymer with phenyl-$C_{71}$-butyric-acid-methyl-ester ($PC_{71}BM$) is in a range between 0.49 and 0.70.

10. The donor-acceptor conjugated polymer of claim 6, wherein a fluorinated donor-acceptor conjugated polymer exhibited a higher fill factor and power conversion efficiency than a hydrogenated donor-acceptor conjugated polymer.

11. A formulation comprising an organic solvent, a fullerene and a donor-acceptor conjugated polymer, wherein the donor-acceptor conjugated polymer comprises one or more repeating units of the following formula:

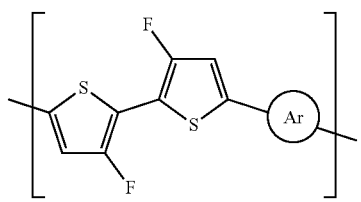

wherein Ar is independently selected from the group consisting of:

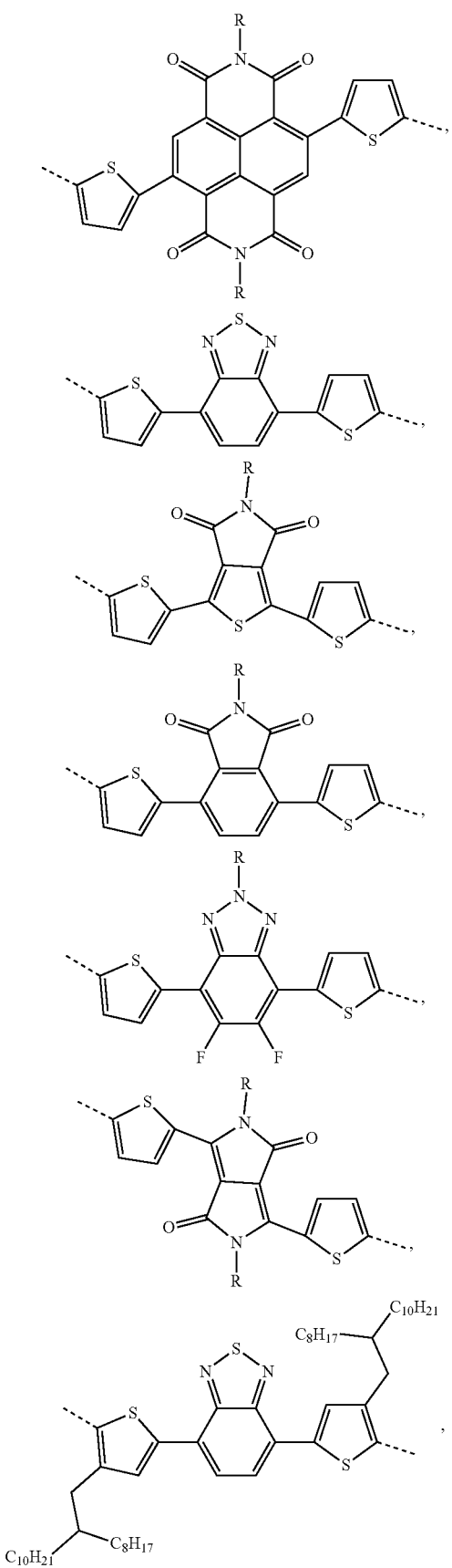

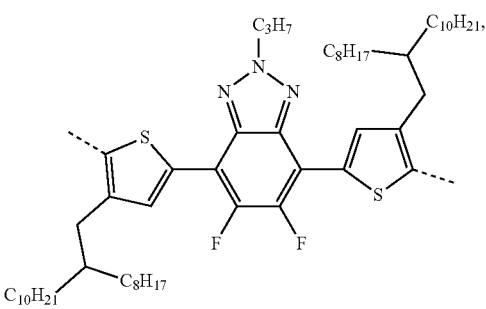

wherein each R is independently selected from the group consisting of straight-chain, branched, and cyclic alkyl with 2-40 C atoms, wherein one or more non-adjacent C atoms are optionally replaced by —O—, —S—, —C(O)—, —C(O)—O—, —O—C(O)—, —O—C(O)—O—, —CR⁰=CR⁰⁰—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein $R^0$ and $R^{00}$ are independently a straight-chain, branched, or cyclic alkyl group.

12. The formulation of claim 11, wherein the fullerene is selected from the group consisting of:

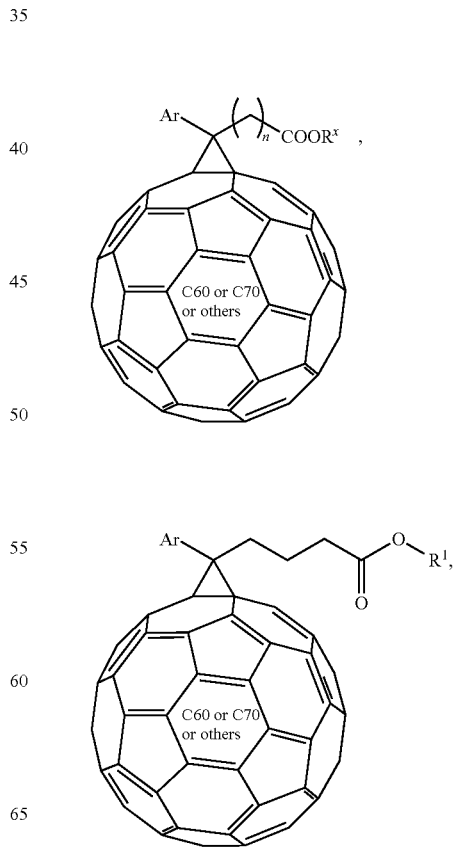

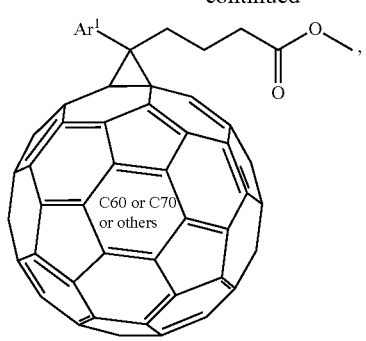
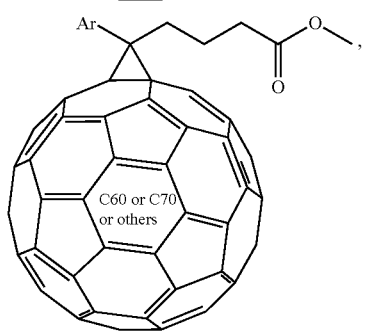
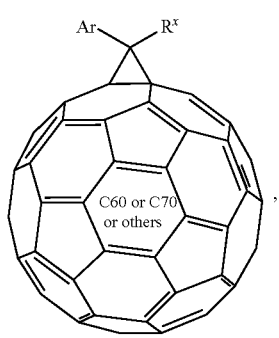
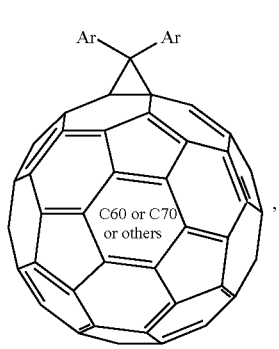
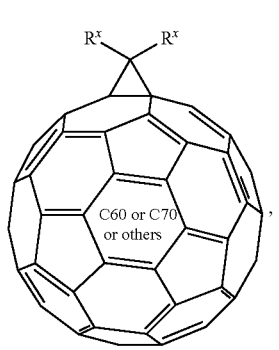
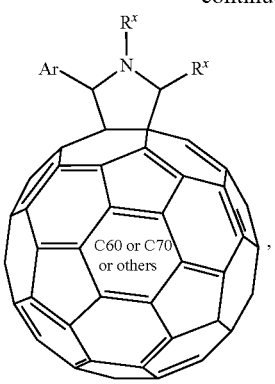
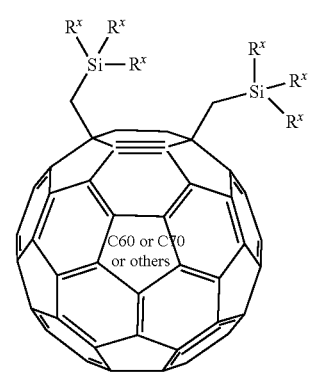
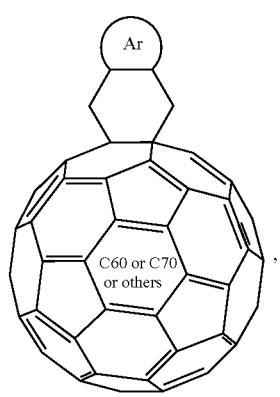
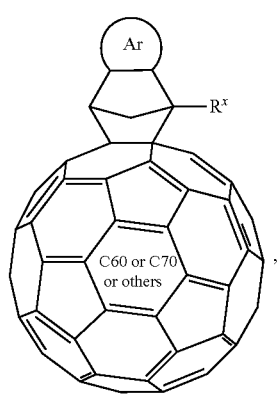

-continued

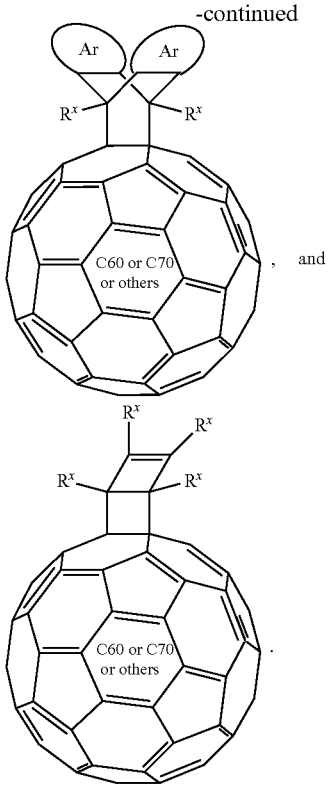, and wherein
- each n=1, 2, 4, 5, or 6;
- each Ar is independently selected from the group consisting of monocyclic, bicyclic, and polycyclic arylene, and monocyclic, bicyclic, and polycyclic heteroarylene, wherein each Ar may contain one to five of said arylene or heteroarylene each of which may be fused or linked;
- each $R^x$ is independently selected from the group consisting of Ar, straight-chain, branched, and cyclic alkyl with 2-40 C atoms, wherein one or more non-adjacent C atoms are optionally replaced by —O—, —S—, —C(O)—, —C(O—)—O—, —O—C(O)—, —O—C(O)—O—, —$CR^o$=$CR^{oo}$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein $R^o$ and $R^{oo}$ are independently a straight-chain, branched, or cyclic alkyl group;
- each $R^1$ is independently selected from the group consisting of straight-chain, branched, and cyclic alkyl with 2-40 C atoms, wherein one or more non-adjacent C atoms are optionally replaced by —O—, —S—, —C(O)—, —O—C(O)—, —O—C(O)—O—, —$CR^o$=$CR^{oo}$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein the number of carbon that R' contains is larger than 1, wherein $R^o$ and $R^{oo}$ are independently a straight-chain, branched, or cyclic alkyl group;
- each $Ar^1$ is independently selected from the group consisting of monocyclic, bicyclic and polycyclic heteroaryl groups, wherein each $Ar^1$ may contain one to five of said heteroaryl groups each of which may be fused or linked;
- each $Ar^2$ is independently selected from aryl groups containing more than 6 atoms excluding H; and wherein the fullerene ball represents a fullerene selected from the group consisting of C60, C70, C84, and other fullerenes.

13. An organic electronic (OE) device comprising a coating or printing ink containing the formulation according to claim 11.

14. The OE device of claim 13, characterized in that the OE device is an organic field effect transistor (OFET) device.

15. The OE device of claim 13, characterized in that the OE device is an organic photovoltaic (OPV) device.

16. A thin film comprising a donor-acceptor conjugated polymer and a fullerene, wherein a solution of the donor-acceptor conjugated polymer exhibits a peak optical absorption spectrum red shift of at least 100 nm when the donor-acceptor conjugated polymer solution is cooled from 140° C. to room temperature, and wherein the donor-acceptor conjugated polymer comprises one or more repeating units of the following formula:

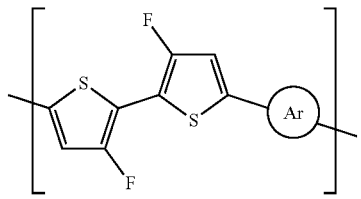

wherein Ar is independently selected from the group consisting of:

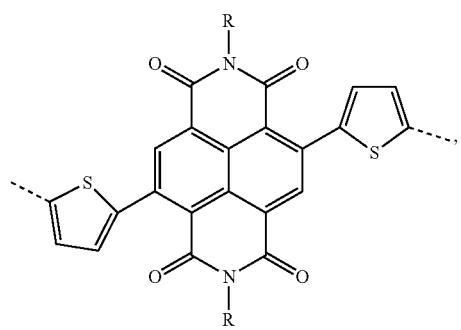

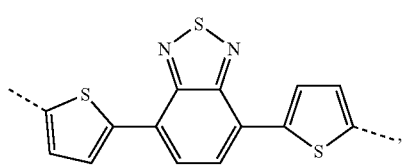

-continued

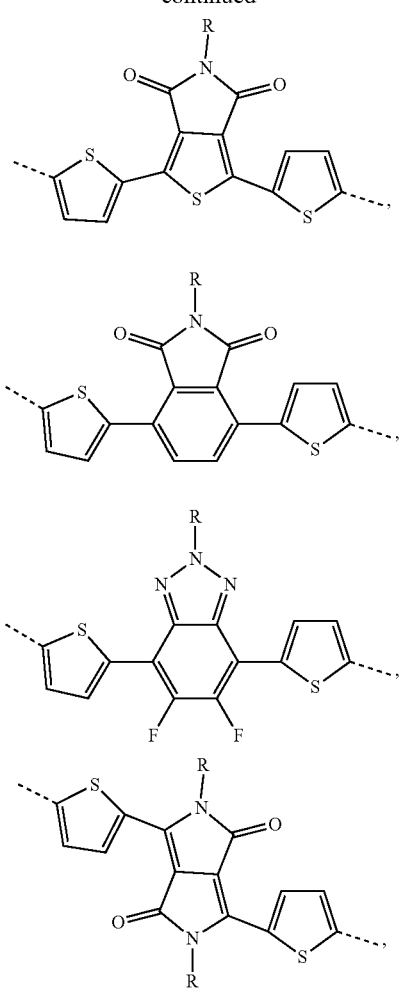

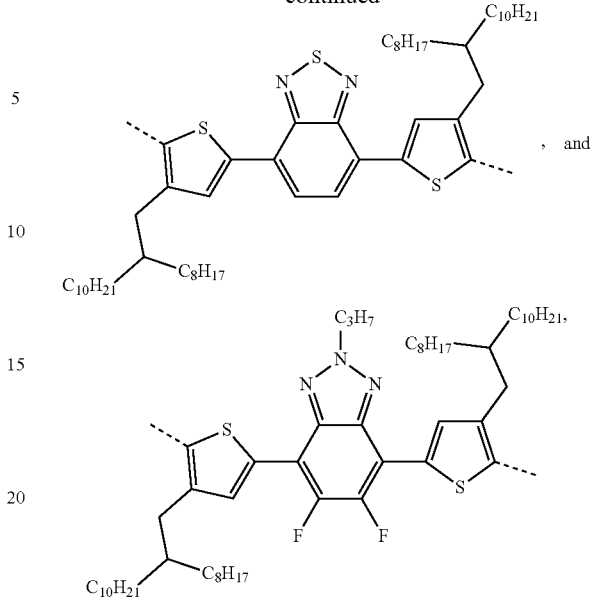

wherein each R is independently selected from the group consisting of straight-chain, branched, and cyclic alkyl with 2-40 C atoms, wherein one or more non-adjacent C atoms are optionally replaced by —O—, —S—, —C(O)—, —C(O—)—O—, —O—C(O)—, —O—C(O)—O—, —CR⁰=CR⁰⁰—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups, wherein $R^O$ and $R^{OO}$ are independently a straight-chain, branched, or cyclic alkyl group.

* * * * *